United States Patent [19]
Gaster et al.

[11] Patent Number: 6,100,272
[45] Date of Patent: Aug. 8, 2000

[54] TETRACYCLIC SPIRO COMPOUNDS AS $5HT_{1B}$ RECEPTOR ANTAGONISTS

[75] Inventors: Laramie Mary Gaster, Bishop's Stortford; Peter Ham, Harlow; Francis David King, Bishops Stortford; Paul Adrian Wyman, Epping, all of United Kingdom

[73] Assignee: SmithKline Beecham p.l.c., Brentford, United Kingdom

[21] Appl. No.: 09/142,988

[22] PCT Filed: Mar. 19, 1997

[86] PCT No.: PCT/EP97/01404

§ 371 Date: Sep. 18, 1998

§ 102(e) Date: Sep. 18, 1998

[87] PCT Pub. No.: WO97/34901

PCT Pub. Date: Sep. 25, 1997

[30] Foreign Application Priority Data

Mar. 20, 1996 [GB] United Kingdom .................... 9605883

[51] Int. Cl.[7] ......................... A61K 31/44; C07D 221/20
[52] U.S. Cl. ................................. 514/278; 546/16; 546/17
[58] Field of Search ......................... 546/16, 17; 514/278

[56] References Cited

U.S. PATENT DOCUMENTS 5,591,849  1/1997  Kato et al. ................................. 544/70

FOREIGN PATENT DOCUMENTS

| | | |
|---|---|---|
| 0 533 266 A1 | 9/1992 | European Pat. Off. . |
| 0 533 268 A1 | 9/1992 | European Pat. Off. . |
| 2761069 | 9/1998 | France . |
| WO 94/15916 | 7/1994 | WIPO . |
| WO 95/17401 | 6/1995 | WIPO . |
| WO 96/11934 | 4/1996 | WIPO . |
| WO 96/19477 | 6/1996 | WIPO . |
| WO 97/10824 | 3/1997 | WIPO . |

OTHER PUBLICATIONS

Rubini et al. "SAynthesis of isoteric methylene–oxy pseudopiptide . . . " Tetrahedron V. 42, p.6039–45, 1986.
Gaster et al. "Preparation of azaspiro compounds as 5HT1B . . . "CA 127:331477, 1997.
Gaster "Preparation of spiroazabicyclic compounds and . . . " CA 128:13254, 1997.

*Primary Examiner*—Ceila Chang
*Attorney, Agent, or Firm*—James M. Kanagy; Charles M. Kinzig

[57] ABSTRACT

Compounds of formula(I)

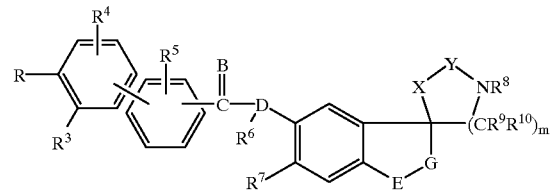

where B is oxygen or sulphur, D is nitrogen, $R^6$ and $R^7$ forms a ring, m is 2, R is a substituted latam ring of formula (i)

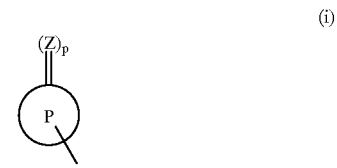

where p is 1, P is a substituted or unsubstituted bicyclic ring containing one or two heteroatoms or P is an unsbustituted or substituted 5- to 7-memebered saturated ring containing one or two heteroatoms; X, Y, Z, E, G, $R^3$, $R^4$, $R^5$, $R^8$, $R^9$, and $R^{10}$ are as defined in the specification.

12 Claims, No Drawings

TETRACYCLIC SPIRO COMPOUNDS AS 5HT$_{1B}$ RECEPTOR ANTAGONISTS

This is a 371 of International Application PCT/EP97/01404, filed Mar. 19, 1997.

The present invention relates to novel piperidine derivatives, processes for their preparation, and pharmaceutical compositions containing them.

EPA 0 533 266/7/8 disclose a series of benzanilide derivatives which are said to possess 5HT$_{1D}$ receptor antagonist activity. PCT/EP/95/04889 discloses further 5HT$_{1D}$ receptor antagonists having a spiropiperidine structure. These compounds are said to be of use in the treatment of various CNS disorders. The 5HT$_{1D\beta}$ receptor has now been reclassified as the 5HT$_{1B}$ receptor (P. R Hartig et al in Trends in Pharmacological Science, 1996, 17, 103–105.

A structurally distinct class of compounds have now been discovered and have been found to exhibit 5HT$_{1B}$ receptor antagonist activity. Compounds of the invention exhibit certain advantages when compared with 5HT$_{1B}$ receptor antagonists known in the art, for example greater selectivity for the 5HT$_{1B}$ receptor over the 5HT$_{1D}$ receptor. In a first aspect, the present invention therefore provides a compound of formula (I) or a salt or N-oxide thereof:

(I)

in which
- R is a group NR$^1$COR$^2$ where R$^1$ is hydrogen, C$_{1-6}$alkyl or together with R$^3$ forms a group (C$_2$)$_k$ where k is 2, 3 or 4 and R$^2$ is hydrogen, C$_{1-6}$alkyl or optionally substituted aryl; or R is an optionally substituted saturated or partially saturated bicyclic heterocyclic ring or monocyclic saturated or partially saturated 5 to 7-membered heterocyclic ring containing 1 to 4 heteroatoms selected from oxygen, nitrogen or sulphur;
- R$^4$ and R$^5$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{11}$, CONR$^{12}$R$^{13}$, NR$^{12}$R$^{13}$ where R$^{11}$, R$^{12}$ and R$^{13}$ are independently hydrogen or C$_{1-6}$alkyl, or R$^4$ and R$^5$ together form a group —(CH$_2$)$_r$—R$^{14}$—(CH$_2$)$_s$— where R$^{14}$ is O, S, CH$_2$ or NR$^{15}$ where R$^{15}$ is hydrogen or C$_{1-6}$alkyl and r and s are independently 0, 1 or 2;
- B is oxygen or sulphur;
- D is nitrogen, carbon or a CH group;
- R$^6$ is hydrogen or C$_{1-6}$alkyl and R$^7$ is hydrogen, C$_{1-6}$alkyl, C$_{1-6}$alkoxy or halogen or R$^6$ together with R$^7$ forms a group —A— where A is (CR$^{16}$R$^{17}$) where t is 2, 3 or 4 and R$^{16}$ and R$^{17}$ are independently hydrogen or C$_{1-6}$alkyl or A is (CR$^{16}$R$^{17}$)$_u$—j where u is 0, 1, 2 or 3 and J is oxygen, sulphur, CR$^{16}$=CR$^{17}$, CR$^{16}$=N, =CR$^{16}$O, =CR$^{16}$S or =CR$^{16}$—NR$^{17}$;
- R$^8$ is hydrogen, C$_{1-6}$alkyl, C$_{3-6}$cycloalkyl, C$_{2-6}$alkenyl or C$_{1-6}$alkylC$_{3-6}$cycloalkyl;
- R$^9$ and R$^{10}$ are independently hydrogen or C$_{1-6}$alkyl;
- E is oxygen, CR$^{18}$R$^{19}$ or NR$^{20}$ where R$^{18}$, R$^{19}$ and R$^{20}$ are independently hydrogen or C$_{1-6}$alkyl or E is S(O)$_v$ where v is 0, 1 or 2;
- G is C=O or (CR$^{21}$R$^{22}$)$_n$ where R$^{21}$ and R$^{22}$ are independently hydrogen or C$_{1-6}$alkyl and n is 1, 2 or 3; X and Y are independently CR$^9$R$^{10}$ where R$^9$ and R$^{10}$ are as defined above; and m is 1, 2 or 3.

C$_{1-6}$alkyl groups, whether alone or as part of another group, may be straight chain or branched. As used herein the term aryl includes phenyl and naphthyl. Heteroaryl groups include thienyl, furyl, pyridyl, pyrimidyl and pyrazinyl groups. Optional substituents for aryl and heteroaryl groups include those groups listed above for R$^4$/R$^5$.

Suitably R is a group NR$^1$COR$^2$ where R$^1$ is hydrogen, C$_{1-6}$alkyl or together with R$^3$ forms a group (C$_2$)$_k$ where k is 2, 3 or 4 and R$^2$ is hydrogen, C$_{1-6}$alkyl or optionally substituted aryl; or R is an optionally substituted saturated or partially saturated bicyclic heterocyclic ring or monocyclic 5 to 7-membered heterocyclic ring. The bicyclic and momocyclic R groups can contain 1 to 4 heteroatoms selected from oxygen, nitrogen or sulphur. Preferred rings are those having an oxo or thioxo moiety such as lactams and thiolactams. The heterocyclic rings can be linked to the remainder of the molecule via a carbon atom or, when present, a nitrogen atom. Suitable substituents for these rings include R$^4$ and R$^5$ groups as defined above.

When R is a group NR$^1$COR$^2$ preferred groups include those where R$^2$ is C$_{1-6}$alkyl, for example methyl, and R$^1$ and R$^3$ form a (CH$_2$)$_3$ group.

Preferably R is an optionally substituted lactam ring of formula (i):

(i)

where Z is oxygen or sulphur;

p is 1 or 2; and

P is an optionally substituted bicyclic ring optionally containing one or two heteroatoms; or P is an optionally substituted 5- to 7-membered saturated or partially saturated ring optionally containing one or two heteroatoms. Preferably in formula (i) Z is oxygen and p is 1.

Even more preferably P is a lactam ring of formula (a):

(a)

where a is 1, 2 or 3. Preferably a is 1 or 2, forming a 5- or 6-membered ring, most preferably a is 1. Other preferred R groups include bicyclic rings of formula (b):

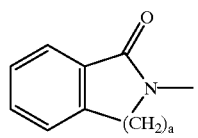

(b)

where a is 1 or 2, preferably where a is 1.

Suitably $R^4$ and $R^5$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkylO$C_{1-6}$alkyl, acyl, aryl, acyloxy, hydroxy, nitro, trifluoromethyl, cyano, $CO_2R^{11}$, $CONR^{12}R^{13}$, $NR^{12}R^{13}$ where $R^{11}$, $R^{12}$ and $R^{13}$ are independently hydrogen or $C_{1-6}$alkyl, or $R^4$ and $R^5$ together form a group —$(CH_2)_r$—$R^{14}$—$(CH_2)_s$— where $R^{14}$ is O, S, $CH_2$ or $NR^{15}$ where $R^{15}$ is hydrogen or $C_{1-6}$alkyl and r and s are independently 0, 1 or 2.

Preferably $R^4$ is $C_{1-6}$alkyl. Preferably the $R^4$ group is ortho with respect to the biphenyl linkage. Most preferably $R^4$ is methyl. Preferably $R^5$ is hydrogen.

Suitably B is oxygen or sulphur. Preferably B is oxygen.

Suitably D is nitrogen, carbon or a CH group. Preferably D is nitrogen.

Suitably $R^6$ is hydrogen or $C_{1-6}$alkyl and $R^7$ is hydrogen, $C_{1-6}$alkyl, $C_{1-6}$alkoxy or halogen or $R^6$ together with $R^7$ forms a group —A— where A is $(CR^{16}R^{17})_t$ where t is 2, 3 or 4 and $R^{16}$ and $R^{17}$ are independently hydrogen or $C_{1-6}$alkyl or A is $(CR^{16}R^{17})_u$—j where u is 0, 1, 2 or 3 and J is oxygen, sulphur, $CR^{16}$=$CR^{17}$, $CR^{16}$=N, =$CR^{16}$O, $CR^{16}$S or =$CR^{16}$—$NR^{17}$. Preferably $R^6$ together with $R^7$ forms a group —A— where A is $(CR^{16}R^{17})_t$ where t is 2 or 3 and $R^{16}$ and $R^{17}$ are both hydrogen. Most preferably $R^6$ together with $R^7$ forms a $(CH_2)_2$ group.

Suitably $R^8$ is hydrogen, $C_{1-6}$alkyl, $C_{3-6}$cycloalkyl, $C_{2-6}$alkenyl or $C_{1-6}$alkyl$C_{3-6}$cycloalkyl. Preferably $R^8$ is $C_{1-6}$alkyl, most preferably $R^8$ is methyl. Preferably m is 2 forming a spiro-piperidine ring.

Suitably $R^9$ and $R^{10}$ are independently hydrogen or $C_{1-6}$alkyl. Preferably $R^9$ and $R^{10}$ are both hydrogen.

Suitably E is oxygen, $CR^{18}R^{19}$ or $NR^{20}$ where $R^{18}$, $R^{19}$ and $R^{20}$ are independently hydrogen or $C_{1-6}$alkyl or E is $S(O)_v$ where v is 0, 1 or 2. Preferably E is oxygen.

Suitably G is C=O or $(CR^{21}R^{22})_n$ where $R^{21}$ and $R^{22}$ are independently hydrogen or $C_{1-6}$alkyl and n is 1, 2 or 3. Preferably G is $CH_2$.

Suitably X and Y are independently $CR^9R^{10}$ where $R^9$ and $R^{10}$ are as defined above. Preferably X and Y are both $CH_2$.

Preferred compounds of the invention include:

5-[2'-Methyl-4'-(2-oxo-1-pyrrolidinyl)biphenyl-4-carbonyl]-1'-methyl-2,3,6,7-tetrahydrospiro[furo[2,3-f]indole-3,4'-piperidine], 1'-Methyl-5-[2'-methyl-4'-(2-oxo-1-piperidinyl)biphenyl-4-carbonyl]-2,3,6,7-tetrahydrospiro[furo[2,3-f]indole-3,4'-piperidine], 5-[4'-(4,5-Dihydro-2-oxooxazol-3-yl)-2'-methylbiphenyl-4-carbonyl]-1'-methyl-2,3,6,7-tetrahydrospiro[furo[2,3-f]indole-3,4'-piperidine], 5-(4'-Acetamido-2'-methylbiphenyl-4-carbonyl)-1'-methyl-2,3,6,7-tetrahydrospiro[furo[2,3-f]indole-3,4'-piperidine], 1'-Methyl-5-[2'-methyl-4'-(2-thioxo-1-pyrrolidinyl)biphenyl-4-carbonyl]-2,3,6,7-tetrahydrospiro[furo[2,3-f]indole-3,4'-piperidine], 5-[4'-(1,1-Dioxo-2,3,4,5-tetrahydroisothiazol-2-yl)-2'-methylbiphenyl-4-carbonyl]-1'-methyl-2,3,6,7-tetrahydrospiro[furo[2,3-f]indole-3,4'-piperidine], 5-[4'-(4,5-Dihydro-2-oxoimidazol-1-yl)-2'-methylbiphenyl-4-carbonyl]-1'-methyl-2,3,6,7-tetrahydrospiro[furo[2,3-f]indole-3,4'-piperidine], 5-[4'-(4,5-Dihydro-3-methyl-2-oxoimidazol-1-yl)-2'-methylbiphenyl-4-carbonyl]-1'-methyl-2,3,6,7-tetrahydrospiro[furo[2,3-f]indole-3,4'-piperidine], 1'-Methyl-5-[2'-methyl-4'-(3-methyl-2-oxopyrrolidin-1-yl)biphenyl-4-carbonyl]-2,3,6,7-tetrahydrospiro[furo[2,3-f]indole-3,4'-piperidine], 5-[4'-(3,3-Dimethyl-2-oxopyrrolidin-1-yl)-2'-methylbiphenyl-4-carbonyl]-1'-methyl-2,3,6,7-tetrahydrospiro[furo[2,3-f]indole-3,4'-piperidine], 5-[4'-(2,3-Dihydro-1-oxoisoindol-2-yl)-2'-methylbiphenyl-4-carbonyl]-1'-methyl-2,3,6,7-tetrahydrospiro[furo[2,3-f]indole-3,4'-piperidine], 5-[2,3'-Dimethyl-4'-(2-oxopyrrolidin-1-yl)biphenyl-4-carbonyl]-1'-methyl-2,3,6,7-tetrahydrospiro[furo[2,3-f]indole-3,4'-piperidine], 1'-Methyl-5-[4'-(2-oxo-1-pyrrolidinyl)-2'-trifluoromethylbiphenyl-4-carbonyl]-2,3,6,7-tetrahydrospiro[furo[2,3-f]indole-3,4'-piperidine], 5-[2'-Chloro-4'-(2-oxo-1-pyrrolidinyl)biphenyl-4-carbonyl]-1'-methyl-2,3,6,7-tetrahydrospiro[furo[2,3-f]indole-3,4'-piperidine], 5-[4-(1-Acetyl-1,2,3,4-tetrahydroquinolin-6-yl)-3-methylbenzoyl]-1'-methyl-2,3,6,7-tetrahydrospiro[furo[2,3-f]indole-3,4'-piperidine], 5-[4-(1-Acetyl-2,3-dihydroindol-5-yl)-3-methylbenzoyl]-1'-methyl-2,3,6,7-tetrahydrospiro[furo[2,3-f]indole-3,4'-piperidine], 1'-Methyl-5-(2'-methyl-4'-(2-oxo-1H-pyrazin-1-yl)biphenyl-4-carbonyl)-2,3,6,7-tetrahydrospiro[furo[2,3-f]indole-3,4'-piperidine], 5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-Ethyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 5-[2'-Methyl-4'-(2-oxopyrrolidin-1-yl)biphenyl-4-carbonyl]-1'-n-propyl-2,3,6,7-tetrahydrospiro[furo[2,3-f]indole-3,4'-piperidine], 1'-Isopropyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-n-Butyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-Cyclopropylmethyl-5-[2'-methyl-4'-(2-oxopyrrolidin-1-yl)biphenyl- 1'-Cyclopropylmethyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-Allyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-Cyclopentyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 2,3,5,6,7,8-Hexahydro-1'-methyl-5-[2'-methyl-4'-(2-oxopyrrolidin-1-yl)biphenyl-4-carbonyl]spiro[furo[2,3-g]quinoline-3,4'-piperidine], 2,3,5,6,7,8-Hexahydro-5-[2'-methyl-4'-(2-oxopyrrolidin-1-yl)biphenyl-4-carbonyl]spiro[furo[2,3-g]quinoline-3,4'-piperidine], cis-2',6'-dimethyl isomer of 5-[2'-Methyl-4'-(2-oxopyrrolidin-1-yl)biphenyl-4-carbonyl]-2,3,6,7-tetrahydro-1',2',6'-trimethylspiro[furo[2,3-f]indole-3,4'-piperidine], 5-[2'-Methoxycarbonyl-4'-(2-oxopyrrolidin-1-yl)biphenyl-4-carbonyl]-1'-methyl-2,3,6,7-tetrahydrospiro[furo[2,3,f]indole-3,4'-piperidine], 5-[2'-Hydroxymethyl-4'-(2-oxopyrrolidin-1-yl)biphenyl-4-carbonyl]-1'-methyl-2,3,6,7-tetrahydrospiro[furo[2,3-f]indole-3,4'-piperidine], 5-[2'-Methoxymethyl-4'-(2-oxopyrrolidin-1-yl)biphenyl-4-carbonyl]-1'-methyl-2,3,6,7-tetrahydrospiro[furo[2,3-f]indole-3,4'-piperidine], 1'-tert-Butyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 2,3-Dihydro-1'-methyl-5-[2'-methyl-4'-(2-oxopyrrolidin-1-yl)biphenyl-4-carbonyl] spiro[furo[3,2-f]indole-3,4'-piperidine], or pharmaceutically acceptable salts thereof.

Particularly preferred compounds of the invention include:

5-[2'-Methyl-4'-(2-oxo-1-pyrrolidinyl)biphenyl-4-carbonyl]-1'-methyl-2,3,6,7-tetrahydrospiro[furo[2,3-f]indole-3,4'-piperidine], 1'-Methyl-5-[2'-methyl-4'-(3-methyl-2-oxopyrrolidin-1-yl)biphenyl-4-carbonyl]-2,3,6,7-tetrahydrospiro[furo[2,3-f]indole-3,4'-piperidine], 1'-Isopropyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 2,3-Dihydro-1'-methyl-5-[2'-methyl-4'-(2-oxopyrrolidin-1-yl)biphenyl-4-carbonyl] spiro[furo[3,2-f]indole-3,4'-piperidine], or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises:

(a) for compounds of formula (I) where D is nitrogen, reaction of a compound of formula (II):

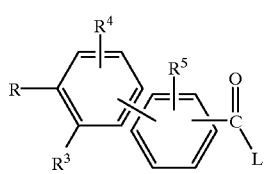

(II)

in which R, $R^3$, $R^4$ and $R^5$ are groups as defined in formula (I) or protected derivatives thereof and L is a leaving group. with a compound of formula (III):

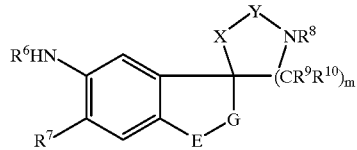

(III)

wherein $R^6$, $R^7$, $R^8$, $R^9$, $R^{10}$, E, G, X, Y, and m are groups as defined in formula (I) or protected derivatives thereof, or (b) for compounds of formula (I) where D is carbon, B is oxygen and $R^6/R^7$ is $=CR^{16}O$, $=CR^{16}S$ or $=CR^{16}$—$NR^{17}$ reaction of a compound of formula (II) as defined above where L is chloro with a compound of formula (IV):

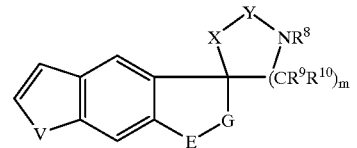

(IV)

wherein $R^6$, $R^7$, $R^8$, $R^9$, $R^{10}$, E, G, X, Y, and m are groups as defined in formula (I) or protected derivatives thereof and V is $NR^{17}$, O or S, and optionally thereafter (a) or (b) in any order:
removing any protecting groups,
converting a compound of formula (I) into another compound of formula (I),
forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazide Preferably the group L is halo, particularly chloro.

Compounds of formulae (II) and (III) are typically reacted together in an inert organic solvent such as DMF, THF or dichloromethane at ambient or elevated temperature in the presence of a base such as an alkali metal hydroxide, triethylamine or pyridine.

Alternatively L is an ester forming group, for example alkyl groups, particularly methyl, such that the resulting esters of formula (II) can be reacted with compounds of formula (III) in the presence of an organo-aluminium reagent such as trimethylaluminium. Such a reaction is typically carried out in the presence of an inert solvent such as toluene.

Intermediate compounds of formula (II) and (III) can be prepared using standard procedures known in the art. Certain intermediate compounds of formula (II), (III) are novel and form a further aspect of the invention.

It will be appreciated to those skilled in the art that it may be necessary to protect certain reactive substituents during some of the above procedures. Standard protection and deprotection techniques can be used such as those described in Greene T. W. 'Protective groups in organic synthesis' New York, Wiley (1981).

For example, primary amines can be protected as phthalimide, benzyl, benzyloxycarbonyl or trityl derivatives. These groups can be removed by conventional procedures well known in the art. Carboxylic acid groups can be protected as esters. Aldehyde or ketone groups can be protected as acetals, ketals, thioacetals or thioketals. Deprotection is achieved using standard conditions.

Compounds of formula (I) can be converted into further compounds of formula (I) using standard procedures. For example compounds where B and/or Z is sulphur can be prepared by reaction of compounds where B and/or Z is oxygen with Lawesson's reagent at elevated temperature in a suitable solvent such as toluene.

$5HT_{1B}$ receptor antagonists, and in particular the compounds of the present invention, are expected to be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1B}$ receptor antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

4'-Amino-2'-methylbiphenyl-4-carboxylic acid

4-Bromo-3-methylaniline (7.40 g, 40 mmol) and 4-carboxybenzeneboronic acid (7.90 g, 48 mmol) were stirred in 1,2-dimethyoxyethane (DME) (150 ml). Anhydrous sodium carbonate (19.0 g, 179 mmol) was dissolved in water (150 ml) and added to the above. The mixture was then purged with a stream of argon for 15 minutes. Tetrakis(triphenylphosphine)palladium (O) (0.25 g, 0.2 mmol) was added, and the mixture was stirred at reflux for 20 h under argon. DME was removed by evaporation under reduced pressure, and the clear residue was acidified with 5M HCl to yield a thick grey suspension. The solid was filtered off, washed with water and dried in vacuo at 60° C., to give the title compound (9.60 g, quantitative).

$^1$H NMR (250 MHz, d$^6$ DMSO) δ (ppm): 8.02 (d, 2H), 7.47 (d, 2H), 7.30 (d, 1H), 7.20 (m, 2H), 2.24 (s, 3H).

DESCRIPTION 2

Methyl 4'-amino-2'-methylbiphenyl-4-carboxylate

Thionyl chloride (10 ml) was added dropwise and cautiously to methanol (200 ml) with stirring. 4'-Amino-2'- methylbiphenyl-4-carboxylic acid (D1) (8.44 g, 37 mmol) was added, and the mixture was then stirred at reflux for 3 h. Solvent was then removed in vacuo to yield the title compound (9.16 g, 89%) as the hydrochloride salt.

$^1$H NMR (HCl salt) (200 MHz, d$^6$ DMSO/CDCl$_3$) δ (ppm): 10.25 (b), 8.06 (d, 2H), 7.41 (d, 2H), 7.30 (m, 3H), 3.92 (s, 3H), 2.28 (s, 3H).

DESCRIPTION 3

Methyl 4'-((4-chlorobutanoyl)amino)-2'-methylbiphenyl-4-carboxylate

Methyl 4'-amino-2'-methylbiphenyl-4-carboxylate (D2) (1.84 g, 7.6 mmol) and triethylamine (2.6 ml, 19 mmol) were stirred in dichloromethane (100 ml) as 4-chlorobutyryl chloride (0.94 ml, 8.4 mmol) was added dropwise. The mixture was stirred for 1 h, vigorously stirred with water for 15 min, acidified with 5M HCl, and separated. The organic portion was washed with water and K$_2$CO$_3$/brine solution, dried (Na$_2$SO$_4$) and evaporated to give a light yellow solid. Chromatography on silica gel, eluting with 0–40% ether/dichloromethane, gave the title compound (1.08 g, 41%) as a light yellow solid.

$^1$H NMR (250 MHz, CDCl$_3$) δ (ppm): 8.08 (d, 2H), 7.3–7.5 (m, 5H), 7.18 (d, 1H), 3.95 (s, 3H), 3.69 (t, 2H), 2.15–2.3 (m, 5H).

DESCRIPTION 4

Methyl 2'-methyl-4'-(2-oxo-1-pyrrolidinyl)biphenyl-4-carboxylate

Methyl 4'-((4-chlorobutanoyl)amino)-2'-methylbiphenyl-4-carboxylate (D3) (1.65 g, 4.8 mmol) was stirred in dry dimethylformamide (DMF) (20 ml) as potassium t-butoxide (0.70 g, 5.7 mmol) was added. The mixture was stirred for 30 min, diluted with ethyl acetate (200 ml), washed successively with brine, water and brine, dried (Na$_2$SO$_4$) and evaporated to give a light brown gum. Chromatography on silica gel, eluting with 0–50% ether/dichloromethane, gave the title compound (1.15 g, 71%) as a light yellow solid.

$^1$H NMR (250 MHz, CDCl$_3$) δ (ppm): 8.08 (d, 2H), 7.57 (d, 1H), 7.49 (dd, 1H), 7.38 (d, 2H), 7.23 (d, 1H), 3.95 (s, 3H), 3.91 (t, 2H), 2.64 (t, 2H), 2.29 (s, 3H), 2.20 (quintet, 2H).

DESCRIPTION 5

1-Acetyl-6-bromo-2,3-dihydro-5-(1-methyl-1,2,3,6-tetrahydro pyridin-4-ylmethoxy)-1-indole The title compound was prepared according to the method of Description 8a in WO 96/19477.

$^1$H NMR (250 MHz, CDCl$_3$) δ ((ppm): 8.42 (s, 1H), 6.72 (s, 1H), 5.80 (br s, 1H), 4.41 (s, 2H), 4.04 (t, 2H), 3.12 (t, 2H), 2.97 (br s, 2H), 2.58 (t, 2H), 2.38 (s, 3H), 2.28 (br s, 2H), 2.18 (s, 3H).

DESCRIPTION 6

5-Acetyl-1-'methyl-2,3,6,7-tetrahydrospirol[furo[2,3-f]indole-3,4'-piperidine]

The title compound was prepared according to the method of Description 8b in WO 96/19477.

$^1$H NMR (250 MHz, CDCl$_3$) δ (ppm): 8.11 (s, 1H), 6.60 (s, 1H), 4.36 (s, 2H), 4.03 (t, 2H), 3.10 (t, 2H), 2.92–2.78 (m, 2H), 2.30 (s, 3H), 2.18 (s, 3H), 2.15–1.90 (m, 4H), 1.80–1.63 (m, 2H).

DESCRIPTION 7

1'-Methyl-2,3,6,7-tetrahydrospiro[furo[2,3-f]indole-3,4'-piperidine]

The title compound was prepared according to the method of Description 8c in WO 96/19477.

$^1$H NMR (250 MHz, CDCl$_3$) δ (ppm): 6.61 (s, 1H), 6.46 (s, 1H), 4.30 (s, 2H), 3.52 (t, 2H), 2.95 (t, 2H), 2.90–2.73 (m, 2H), 2.31 (s, 3H), 2.10–1.85 (m, 4H), 1.82–1.60 (m, 2H).

DESCRIPTION 8

Methyl 4'-((5-chloropentanoyl)amino)-2'-methylbiphenyl-4-carboxylate

Similar procedure to Description 3 from D2 and 5-chlorovaleryl chloride.

$^1$H NMR (250 MHz, CDCl$_3$) δ (ppm): 8.06 (d, 2H), 7.49 (s, 1H), 7.3–7.45 (m, 3H), 7.2 (m, 2H), 3.93 (s, 3H), 3.60 (m, 2H), 2.43 (m, 2H), 2.26 (s, 3H), 1.9 (m, 4H).

DESCRIPTION 9

2-Chloroethyl N-[4'-(methoxycarbonyl)-2-methylbiphenyl-4-yl] carbamate

Similar procedure to Description 3 from D2 and 2-chloroethyl chloroformate, but using pyridine as base.

$^1$H NMR (200 MHz, CDCl$_3$) δ (ppm): 8.07 (d, 2H), 7.25–7.4 (m, 4H), 7.18 (d, 1H), 6.80 (s, 1H), 4.45 (t, 2H), 3.95 (s, 3H), 3.76 (t, 2H), 2.26 (s, 3H).

DESCRIPTION 10

Methyl 2'-methyl-4'-(2-oxo-1-piperidinyl)biphenyl-4-carboxylate

Similar procedure to Description 4 from D5.

$^1$H NMR (250 MHz, CDCl$_3$) δ (ppm): 8.09 (d, 2H), 7.40 (d, 2H), 7.26 (d, 1H), 7.1–7.2 (m, 2H), 3.95 (s, 3H), 3.69 (m, 2H), 2.6 (m, 2H), 2.26 (s, 3H), 1.98 (m, 4H).

DESCRIPTION 11

Methyl 4'-(4,5-dihydro-2-oxooxazol-3-yl)-2'-methylbiphenyl-4-carboxylate

Similar procedure to Description 4 from D6.

$^1$H NMR (200 MHz, CDCl$_3$) δ (ppm): 8.08 (d, 2H), 7.3–7.5 (m, 4H), 7.24 (d, 1H), 4.51 (dd, 2H), 4.10 (dd, 2H), 3.95 (s, 3H), 2.29 (s, 3H).

DESCRIPTION 12

N-[4-Bromo-3-methylphenyl]-acetamide

A stirred solution of 4-bromo-3-methylaniline (3.0 g, 0.016 mole) and triethylamine (4.5 fml, 0.032 mole) in dichloromethane (30 ml) at 0° C. was treated with acetyl chloride (1.2 ml, 0.017 mole) and allowed to warm to room temperature over 1 h. The mixture was washed with water, then 5M HCl acid and dried (Na$_2$SO$_4$), then concentrated in vacuo to afford the title compound as a pale yellow solid (3.07 g, 83%).

$^1$H NMR (200 MHz, CDCl$_3$) δ (ppm): 7.50–7.35 (m, 2H), 7.19 (dd, 1H), 2.36 (s, 3H), 2.16 (s, 3H).

DESCRIPTION 13

4'-Acetamido-2'-methylbiphenyl-4-carboxylic acid

The title compound was prepared from N-[4-bromo-3-methylphenyl]-acetamide (D12) as a white solid (66%).

¹H NMR (200 MHz, d⁶DMSO) δ (ppm): 12.8 (br s, 1H), 9.98 (s, 1H), 7.98 (d, 2H), 7.55–7.40 (m, 4H), 7.16 (d, 1H), 2.20 (s, 3H), 2.05 (s, 3H)

DESCRIPTION 14

Methyl 2'-methyl-4'-(2-thioxo-1-pyrrolidinyl) biphenyl-4-carboxylate

Methyl 2'-methyl-4'-(2-oxo-1-pyrrolidinyl)biphenyl-4-carboxylate (D4, 200 mg, 0.647 mmol) was dissolved in toluene (25 ml) and Lawesson's reagent (130 mg, 0.324 mmol) was added. The solution was heated at 75° C. under argon for 1.5 hrs, then concentrated in vacuo. The resultant pale yellow solid was filtered through a neutral alumina column eluting with ether to remove excess Lawesson's reagent, then purified by column chromatography on silica gel eluting with ether to afford the title compound as a yellow solid (128 mg, 61%).

¹H NMR (250 MHz, CDCl₃) δ (ppm): 8.10 (d, 2H), 7.48–7.37 (m, 4H), 7.31 (d, 1H), 4.16 (t, 2H), 3.96 (s, 3H), 3.28 (t, 2H), 2.29 (s, 3H), 2.36–2.18 (m, 2H).

DESCRIPTION 15

Methyl 4'-[(3-chloropropylsulphonyl)amino]-2'-methylbiphenyl-4-carboxylate

This was prepared following the procedure of Description 3, using 3-chloropropanesulphonyl chloride. Chromatography of the crude product on silica, eluting with 0–100% ether in dichloromethane, gave the title compound as a colourless syrup (44%).

¹H NMR (200 MHz, CDCl₃) δ (ppm): 8.09 (d, 2H), 7.37 (d, 2H), 7.1–7.3 (m, 3H), 6.81 (s, 1H), 3.95 (s, 3H), 3,69 (t, 2H), 3.35 (t, 2H), 2.34 (m, 2H), 2.27 (s, 3H).

DESCRIPTION 16

Methyl 4'-(1,1-dioxo-2,3,4,5-tetrahydroisothiazol-2-yl)-2'-methylbiphenyl-4-carboxylate This was prepared from methyl 4'-[(3-chloropropanesulphonyl)amino]2'-methylbiphenyl-4-carboxylate (D15), following the procedure of Description 4. This gave the title compound as a light yellow solid (88%).

¹H NMR (250 MHz, CDCl₃) δ (ppm): 8.07 (d, 2H), 7.37 (d, 2H), 7.1–7.3 (m, 3H), 3.94 (s, 3H), 3.83 (t, 2H), 3.43 (t, 2H), 2.57 (quintet, 2H), 2.28 (s, 3H).

DESCRIPTION 17

N-(2-Chloroethyl)-N'-(4'-methoxycarbonyl-2-methylbiphenyl-4-yl)urea

Methyl 4'-amino-2'-methylbiphenyl-4-carboxylate (D2) (1.00 g, 4.1 mmol) and 2-chloroethylisocyanate (0.39 ml, 4.5 mmol) were stirred in dichloromethane (20 ml) for 72 h. The suspension was then diluted with toluene (20 ml), and the solid was filtered off and dried. This gave the title compound (0.99 g, 69%) as a cream solid.

¹H NMR (200 MHz, d⁶DMSO) δ (ppm): 8.68 (s, 1H), 7.94 (d, 2H), 7.41 (d, 2H), 7.30 (m, 2H), 7.06 (d, 1H), 6.42 (t, 1H), 3.82 (s, 3H), 3.62 (t, 2H), 3.40 (t, 2H), 2.16 (s, 3H)

DESCRIPTION 18

Methyl 4'-(4,5-dihydro-2-oxoimidazol-1-yl)-2'-methylbiphenyl-4-carboxylate

This was prepared from N-(2-chloroethyl)-N'-(4'-methoxycarbonyl-2-methylbiphenyl-4-yl)urea (D17), following the procedure of Description 4. The product was isolated by dilution of the reaction mixture with water, filtration and drying. This gave the title compound as a cream solid (90%).

¹H NMR (200 MHz, d⁶DMSO) δ (ppm): 7.95 (d, 2H), 7.45 (m, 4H), 7.13 (d, 1H), 6.96 (s, 1H), 3.82 (s, 3H and t, 2H), 3.37 (t, 2H), 2.19 (s, 3H).

DESCRIPTION 19

Methyl 4'-(4,5-dihydro-3-methyl-2-oxoimidazol-1-yl)-2'-methylbiphenyl4-carboxylate Methyl 4'-(4,5-dihydro-2-oxoimidazol-1-yl)-2'-methylbiphenyl-4-carboxylate (D18) (0.208 g, 0.67 mmol) was stirred in dry DMF (5 ml). Potassium t-butoxide (0.10 g, 0.82 mmol) and iodomethane (0.065 ml, 1.0 mmol) were added. The mixture was stirred for 1 h, diluted with ethyl acetate, washed with water and brine, dried (Na₂SO₄) and evaporated to give a gum. Chromatography on silica eluting with 50% ether in dichloromethane gave the title compound (0.205 g, 94%) as a white solid.

¹H NMR (200 MHz, CDCl₃) δ (ppm): 7.98 (d, 2H), 7.43 (d, 1H), 7.30 (m, 1H and d, 2H), 7.11 (d, 1H), 3.85 (s, 3H), 3.73 (dd, 2H), 3.39 (dd, 2H), 2.82 (s, 3H), 2.20 (s, 3H).

DESCRIPTION 20

1-(4-Bromo-3-methylphenyl)-3-methylpyrrolidin-2-one

A stirred solution of 4-bromo-3-methylaniline (1.0 g, 0.0054 mole) in toluene (80 ml) at 25° C. under argon was treated with trimethylaluminium (2.7 ml of 2M solution in toluene, 0.0054 mole). After 15 mins the mixture was treated with a-methyl-y-butyrolactone (0.50 ml, 0.0054 mole) and then heated under reflux for 0.75 h. The reaction mixture was allowed to cool, treated with 10% aqueous NaOH solution (50 ml) and concentrated in vacuo to remove the toluene. The residual aqueous was extracted with dichloromethane and the extract dried (Na₂SO₄) and concentrated in vacuo to leave a white solid (1.45 g). A portion of this material (0.95 g, 0.0034 mole) was dissolved in dry THF (60 ml), treated with triphenylphosphine (0.99 g, 0.0038 mole), followed by diethyl azodicarboxylate (0.60 ml, 0.0038 mole). The mixture was stirred at 25° C. for 2 h, then concentrated in vacuo and chromatographed on silica gel eluting with dichloromethane to afford the title compound as a pink solid (85%).

¹H NMR (250 MHz, CDCl₃) δ (ppm): 7.60 (d, 1H), 7.49 (d, 1H), 7.32 (dd, 1H), 3.80–3.70 (m, 2H), 2.75–2.57 (m, 1H), 2.45–2.28 (m, 1H), 2.40 (s, 3H), 1.85–1.67 (m, 1H), 1.30 (d, 3H).

DESCRIPTION 21

2'-Methyl-4'-(3-methyl-2-oxopyrrolidin-1-yl) biphenyl-4-carboxylic acid

The title compound was prepared from 1-(4-bromo-3-methylphenyl)-3-methylpyrrolidin-2-one (D20) following a similar procedure to Description 1, as a white solid (85%).

¹H NMR (250 MHz, d⁶DMSO) δ (ppm): 8.00 (d, 2H), 7.67–7.58 (m, 2H), 7.46 (d, 2H), 7.23 (d, 1H), 3.85–3.74 (m, 2H), 2.75–2.55 (m, 1H), 2.40–2.18 (m, 1H), 2.26 (s, 3H), 1.80–1.60 (m, 1H), 1.17 (d, 3H).

DESCRIPTION 22

Methyl 2'-methyl-4'-(3-methyl-2-oxopyrrolidin-1-yl) biphenyl-4-carboxylate

A stirred solution of 2'-methyl-4'-(3-methyl-2-oxopyrrolidin-1-yl)biphenyl-4-carboxylic acid (D21, 0.35 g, 0.0011 mole) in DMF (5 ml) at 25° C. was treated with anhydrous potassium carbonate (0.27 g, 0.0020 mole) and iodomethane (0.08 ml, 0.0014 mole). The mixture was stirred for 3 hours, then diluted with water (100 ml) and extracted with ethyl acetate (2×100 ml). The combined extract was washed with water (2×100 ml), then dried ($Na_2SO_4$) and concentrated in vacuo to afford the title compound as a beige solid (0.35 g, 99%).

$^1$H NMR (250 MHz, $CDCl_3$) δ (ppm): 8.08 (d, 2H), 7.62 (d, 1H), 7.50 (dd, 1H), 7.38 (d, 2H), 7.23 (d, 1H), 3.95 (s, 3H), 3.87–3.77 (m, 2H), 2.80–2.60 (m, 1H), 2.48–2.32 (m, 1H), 2.28 (s, 3H), 1.90–1.70 (m, 1H), 1.32 (d, 3H).

DESCRIPTION 23

1-(4-Bromo-3-methylphenyl)-3,3-dimethylpyrrolidin-2-one

The title compound was prepared from 4-bromo-3-methylaniline and α,α-dimethyl-γ-butyrolactone following a similar procedure to Description 20, as a pink solid (53%).

$^1$H NMR (250 MHz, $CDCl_3$) δ (ppm): 7.64 (d, H), 7.49 (d, 1H), 7.32 (dd, 1H), 3.73 (t, 2H), 2.40 (s, 3H), 2.00 (t, 2H), 1.23 (s, 6H).

DESCRIPTION 24

4'-(3,3-Dimethyl-2-oxopyrrolidin-1-yl)-2'-methylbiphenyl-4-carboxylic acid

The title compound was prepared from 1-(4-bromo-3-methylphenyl)-3,3-dimethylpyrrolidin-2-one (D23) following a similar procedure to Description 1, as a white solid (39%).

$^1$H NMR (250 MHz, $d^6$DMSO) δ (ppm): 8.00 (d, 2H), 7.68–7.58 (m, 2H), 7.47 (d, 2H), 7.23 (d, 1H), 3.80 (t, 2H), 2.25 (s, 3H), 1.97 (t, 2H), 1.14 (s, 6H).

DESCRIPTION 25

Methyl 4'-(3,3-dimethyl-2-oxopyrrolidin-1-yl)-2'-methylbiphenyl-4-carboxylate

The title compound was prepared from 4'-(3,3-dimethyl-2-oxopyrrolidin-1-yl)-2-methylbiphenyl-4-carboxylic acid (D24) following a similar procedure to Description 20, as a beige solid (91%).

$^1$H NMR (250 MHz, $CDCl_3$) δ (ppm): 8.08 (d, 2H), 7.67 (d, 1H), 7.53 (dd, 1H), 7.40 (d, 2H), 7.23 (d, 1H), 3.95 (s, 3H), 3.80 (t, 2H), 2.29 (s, 3H), 2.03 (t, 2H), 1.26 (s, 6H)

DESCRIPTION 26

2-(4-Bromo-3-methylphenyl)-2,3-dihydroisoindol-1-one

The title compound was prepared from 4-bromo-3-methylaniline and phthalide using a similar procedure to Description 20, as a white solid (76%).

$^1$H NMR (250 MHz, $CDCl_3$) δ (ppm): 7.90 (d, 1H), 7.80 (d, 1H), 7.65–7.45 (m, 5H), 4.82 (s, 2H), 2.44 (s, 3H).

DESCRIPTION 27

4'-(2,3-Dihydro-1-oxoisoindol-2-yl)-2'-methylbiphenyl4-carboxylic acid

The title compound was prepared from 2-(4-bromo-3-methylphenyl)-2,3-dihydroisoindol-1-one (D26) using a similar procedure to Description 1, as a white solid (100%).

$^1$H NMR (250 MHz, $d^6$DMSO) δ (ppm): 8.02 (d, 2H), 7.89 (dd, 1H), 7.85 (d, 1H), 7.80 (d, 1H), 7.72–7.65 (m, 2H), 7.62–7.50 (m, 1H), 7.50 (d, 2H), 7.32 (d, 1H), 5.05 (s, 2H), 2.30 (s, 3H).

DESCRIPTION 28

Methyl 4'-(2,3-dihydro-1-oxoisoindol-2-yl)-2'-methylbiphenyl-4-carboxylate

The title compound was prepared from 4'-(2,3-dihydro-1-oxoisoindol-2-yl)-2'-methylbiphenyl-4-carboxylic acid (D27) using a similar procedure to Description 22, as a white solid (74%).

$^1$H NMR (250 MHz, $CDCl_3$) δ (ppm): 8.10 (d, 2H), 7.95 (d, 1H), 7.83 (d, 1H), 7.74 (dd, 1H), 7.68–7.48 (m, 3H), 7.42 (d, 2H), 7.30 (d, 1H), 4.90 (s, 2H), 3.95 (s, 3H), 2.35 (s, 3H).

DESCRIPTION 29

4-Borono-3-methylbenzoic acid

A stirred solution of 4-bromo-3-methylbenzoic acid (5.0 g, 0.02 mole) in dry THF (250 ml) at −78° C. under argon was treated with 1.6M n-butyllithium in hexane (36.3 ml, 0.05 mole). The mixture changed from a clear solution to an orange suspension. This was stirred at −78° C. for 0.25 h, then treated with triisopropyl borate (13.4 ml, 0.05 mole) and stirred at −78° C. for a further 1 h. The mixture was allowed to warm to room temp. and stirred for 19 h, then treated with water (25 ml) and concentrated in vacuo. The residue was chromatographed on silica gel eluting with 10% methanol/dichloromethane to afford the title compound as a white solid (2.63 g, 67%).

$^1$H NMR (200 MHz, $d^6$DMSO) δ (ppm): 7.72–7.63 (m, 2H), 7.50 (d, 1H), 2.43 (s, 3H). (carboxylic and boronic acid protons not observed)

DESCRIPTION 30

4'-Amino-2,3'-dimethylbiphenyl-4-carboxylic acid

The title compound was prepared from 4-bromo-2-methylaniline and 4-borono-3-methylbenzoic acid (D29) using a similar procedure to Description 1 as a brown solid (41%). This was used in the next step without further purification.

DESCRIPTION 31

Methyl 4'-amino-2,3'-dimethylbiphenyl-4-carboxylate

The title compound was prepared from 4'-amino-2,3'-dimethylbiphenyl-4-carboxylic acid (D30) using a similar procedure to Description 32, as a yellow oil (96%).

$^1$H NMR (250 MHz, $CDCl_3$) δ (ppm): 7.94 (s, 1H), 7.87 (d, 1H), 7.27 (d, 1H), 7.05–6.97 (m, 2H), 6.72 (d, 1H), 3.92 (s, 3H), 3.75 (br s, 2H), 2.33 (s, 3H), 2.20 (s, 3H).

DESCRIPTION 32

Methyl 2,3'-dimethyl4'-(2-oxopyrrolidin-1-yl) biphenyl-4-carboxylate

The title compound was prepared from methyl 4'-amino-2,3'-dimethylbiphenyl-4-carboxylate (D3) following similar procedures to Description 3 and 4, as a beige solid (46%).

$^1$H NMR (200 MHz, $CDCl_3$) δ ((ppm): 8.00–7.85 (m, 2H), 7.32–7.17 (m, 4H), 3.93 (s, 3H), 3.78 (t, 2H), 2.62 (t, 2H), 2.40–2.17 (m, 2H), 2.34 (s, 3H), 2.30 (s, 3H).

DESCRIPTION 33

4'-Amino-2'-trifluoromethylbiphenyl-4-carboxylic acid

A stirred solution of 5-amino-2-bromobenzotrifluoride (2.5 g, 0.01 mol) in DME (60 ml) and water (60 ml) was treated with 4-boronobenzoic acid (1.65 g, 0.01 mol) and $Na_2CO_3$ (4.2 g, 0.04 mol). The mixture was degassed with argon for 15 mins, treated with tetrakis (triphenylphosphine) palladium (O) (230 mg, 0.2 mmol) and heated at reflux under argon for 18 hrs. The mixture was concentrated in vacuo to approx. 50% volume and the aqueous residue treated with 10% aqueous $Na_2CO_3$ solution and washed with ethyl acetate. The aqueous layer was separated, acidified with 5M HCl and concentrated in vacuo to afford an off-white solid containing the title compound. This was used in the next step without further purification.

DESCRIPTION 34

Methyl 4'-amino-2'-trifluoromethylbiphenyl-4-carboxylate

Crude 4'-amino-2'-trifluoromethylbiphenyl-4-carboxylic acid (D33, 0.31 g, 0.078 mol) was dissolved in methanol (200 ml) and treated with conc. $H_2SO_4$ acid (1 ml). The mixture was heated at reflux under argon for 2 hrs, then concentrated in vacuo. The resultant yellow solid was basified with 10% aqueous $Na_2CO_3$ solution, extracted with dichloromethane, then the extract dried ($Na_2SO_4$) and concentrated in vacuo. The resultant yellow solid was purified by preparative TLC on silica gel plates eluting with 1:1 pet ether/ether to afford the title compound as an off-white solid (161 mg, 50%).

$^1$H NMR (250 MHz, $CDCl_3$) δ (ppm): 7.97 (d, 2H), 7.30 (d, 2H), 7.01 (d, 1H), 6.96 (d, 1H), 6.77 (dd, 1H), 3.88 (br s, 5H).

DESCRIPTION 35

Methyl 4'-(4-chlorobutanoyl)amino-2'-trifluoromethylbiphenyl-4-carboxylate

The title compound was prepared from methyl 4'-amino-2'-trifluoromethylbiphenyl-4-carboxylate (D34) using a similar procedure to Description 3, as a beige solid (47%).

$^1$H NMR (250 MHz, $CDCl_3$) δ (ppm): 8.08 (d, 2H), 7.90 (s, 1H), 7.82 (dd, 1H), 7.50 (s, 1H), 7.39 (d, 2H), 7.30 (d, 1H), 3.95 (s, 3H), 3.70 (t, 2H), 2.64 (t, 2H), 2.24 (m, 2H).

DESCRIPTION 36

Methyl 4'-(2-oxopyrrolidin-1-yl)-2'-trifluoromethylbiphenyl-4-carboxylate

The title compound was prepared from methyl 4'-(4-chlorobutanoyl)amino-2'-trifluoromethylbiphenyl-4-carboxylate (D35) using a similar procedure to Description 4, as a red oil (38%).

$^1$H NMR (250 MHz, $CDCl_3$) δ (ppm): 8.08 (d, 2H), 7.95 (s, 2H), 7.40 (d, 2H), 7.33 (d, 1H), 3.95 (m, 5H), 2.69 (t, 2H), 2.24 (m, 2H).

DESCRIPTION 37

4'-Amino-2'-chlorobiphenyl-4-carboxylic acid

The title compound was prepared from 4-bromo-3-chloroaniline using a similar procedure to Description 1 as an off-white solid (72%).

$^1$H NMR (250 MHz, $d^6$DMSO) δ (ppm): 8.00 (d, 2H), 7.53 (d, 2H), 7.37 (d, 1H), 7.26 (d, 1H), 7.13 (dd, 1H).

DESCRIPTION 38

Methyl 4'-amino-2'-chlorobiphenyl-4-carboxylate

The title compound was prepared from 4'-amino-2'-chlorobiphenyl-4-carboxylic acid (D37) using a similar procedure to Description 34, as a beige solid (75%).

$^1$H NMR (250 MHz, $CDCl_3$) δ (ppm): 8.06 (d, 2H), 7.50 (d, 2H), 7.13 (d, 1H), 6.80 (d, 1H), 6.64 (dd, 1H), 3.94 (s, 3H), 3.83 (br s, 2H).

DESCRIPTION 39

Methyl 2'-chloro-4'-(4-chlorobutanoyl) aminobiphenyl-4-carboxylate

The title compound was prepared from methyl 4'-amino-2'-chlorobiphenyl-4-carboxylate (D38) using a similar procedure to Description 3, as a beige solid (85%).

$^1$H NMR (200 MHz, $CDCl_3$) δ (ppm): 8.10 (d, 2H), 7.78 (d, 1H), 7.51 (d, 2H), 7.45 (d, 1H), 7.37 (br s, 1H), 7.30 (d, 1H), 3.95 (s, 3H), 3.69 (t, 2H), 2.61 (t, 2H), 2.33–2.08 (m, 2H).

DESCRIPTION 40

Methyl 2'-chloro-4'-(2-oxopyrrolidin-1-yl)biphenyl-4-carboxylate

The title compound was prepared from methyl 2'-chloro-4'-(4-chlorobutanoyl) aminobiphenyl-4-carboxylate (D39) using a similar procedure to Description 4, as a pale brown solid (46%).

$^1$H NMR (200 MHz, $CDCl_3$) δ (ppm): 8.10 (d, 2H), 7.78 (d, 1H), 7.68 (dd, 1H), 7.53 (d, 2H), 7.34 (d, 1H), 4.04–3.80 (m, 5H), 2.67 (t, 2H), 2.36–2.10 (m, 2H).

DESCRIPTION 41

1-Acetyl-1,2,3,4-tetrahydro-6-trifluoromethanesulphonyloxyquinoline

To a stirred solution of 1-acetyl-6-hydroxy-1,2,3,4-tetrahydroquinoline (2.36 g, 0.012 mol) and pyridine (2.0 ml, 0.025 mol) in THF (80 ml) under argon was added triflic anhydride (2.0 ml, 0.014 mol). The reaction mixture was stirred at room temperature for 3 days and after additional amounts of triflic anhydride (6 ml, 0.041 mol) and pyridine (6 ml, 0.074 mol) had been added, was concentrated in vacuo. The resultant brown gum was treated with 10% aqueous $Na_2CO_3$ solution and extracted with dichloromethane. The extract was dried ($Na_2SO_4$) and concentrated in vacuo. The crude product was purified by chromatography on silica gel, eluting with ethyl acetate to afford the title compound as an orange oil (430 mg, 11%).

$^1$H NMR (250 MHz, $CDCl_3$) δ (ppm): 7.50 (br s, 1H—low integration), 7.15–7.03 (m, 2H 3.79 (t, 2H), 2.80 (t, 2H), 2.25 (s, 3H), 2.00 (quintet, 2H).

DESCRIPTION 42

4-(1-Acetyl-1,2,3,4-tetrahydroquinolin-6-yl)-3-methylbenzoic acid

4-Borono-3-methylbenzoic acid (D29) (220 mg, 1.2 mmol), 1-acetyl-1,2,3,4-tetrahydro-6-trifluoromethanesulphonyloxyquinoline (D41, 410 mg, 1.25 mmol), lithium chloride (150 mg, 3.6 mmol) and sodium carbonate (505 mg, 4.7 mmol) were dissolved in a mixture of water (10 ml) and dimethoxyethane (10 ml). The suspension was degassed with argon for 15 mins and then treated with tetrakis (triphenylphosphine)palladium (O) (68 mg). The reaction mixture was heated at reflux for 28 hrs, then concentrated in vacuo. The residue was treated with 10% aqueous $Na_2CO_3$ solution and washed with ethyl acetate. The aqueous layer was acidified with 5M HCl and the resultant precipitate was filtered off and dried to afford the title compound as a light brown solid (386 mg, 100%).

$^1$H NMR (250 MHz, $d^6$DMSO) δ (ppm): 7.87 (s, 1H), 7.82 (d, 1H), 7.60 (br, 1H), 7.33 (d, 1H), 7.26–7.12 (m, 2H), 3.73 (t, 2H), 2.78 (t, 2H), 2.33 (s, 3H), 2.22 (s, 3H), 2.01–1.82 (m, 2H).

DESCRIPTION 43

4-(1-Acetyl-2,3-dihydroindol-5-yl)-3-methylbenzoic acid

The title compound was prepared using a similar procedure to that described in D1 from 1-acetyl-5-bromoindoline to afford the title compound as a purple solid (25%).

$^1$H NMR (250 MHz, $d^6$DMSO) δ (ppm): 8.09 (d, 1H), 7.84 (s, 1H), 7.78 (d, 1H), 7.26 (m, 2H), 7.13 (d, 1H), 4.13 (t, 2H), 3.19 (t, 2H), 2.29 (s, 3H), 2.18 (s, 3H).

DESCRIPTION 44

1-(4-Bromo-3-methylphenyl)-1-pyrazin-2-one

The title compound was prepared from N-benzyloxycarbonylglycine (12 g, 0.057 mol) and 4-bromo-3-methylaniline (10.68 g, 0.057 mol) using similar methodology to that described by M. Mano et al, *Chem. Pharm. Bull.* (1980), 28 (9), 2734–47, as a white solid (1.76 g, 12% over 3 steps).

$^1$H NMR (200 MHz, $CDCl_3$) δ (ppm): 8.25 (s, 1H), 7.68 (d, 1H), 7.39 (d, 1H), 7.3 (s, 1H), 7.16–7.05 (m, 2H), 2.44 (s, 3H).

DESCRIPTION 45

2'-Methyl-4'-(2-oxo-1-pyrazin-1-yl)biphenyl-4-carboxylic acid

A stirred solution of 1-(4-bromo-3-methylphenyl)-1H-pyrazin-2-one (D44, 1.4 g; 5.28 mmole), 4-boronobenzoic acid (877 mg; 5.28 mmole) and anhydrous sodium carbonate (3.69 g; 0.0348 mole) in 1:1 dimethoxyethane: water (200 ml) (previously degassed with argon), was treated under argon, with tetrakis(triphenylphosphine)palladium (O) (250 mg), and the mixture was heated under reflux for 20 h. The organic solvent was evaporated under reduced pressure, the aqueous phase was basified using 5% aqueous NaOH solution, and washed twice with ethyl acetate. The basic aqueous phase was acidified with 5M HCl acid giving a copious precipitate, which was filtered, washed with water and dried in vacuo to give the title compound (790 mg, 49%).

$^1$H NMR (250 MHz, $d^6$DMSO) δ (ppm): 13.05 (br s, 1H), 8.15 (s, 1H), 8.03 (d, 2H), 7.7 (d, 1H), 7.52 (d, 2H), 7.5–7.35 (m, 4H), 2.3 (s, 3H).

DESCRIPTION 46

1-(4-Bromo-3-methylphenyl)pyrrolidin-2-one

A stirred solution of 4-bromo-3-methylaniline (50.3 g, 0.27 mole) and triethylamine (41.1 ml, 0.30 mole) in THF (250 ml) at 0° C. under argon was treated dropwise with 4-chlorobutyryl chloride (33.4 ml, 0.30 mole). The mixture was stirred for 1 hour at 0–5° C., then potassium t-butoxide (82.5 g, 0.74 mole) was added portionwise over 20 minutes, maintaining temperature below 25° C. The reaction mixture was stirred at 25° C. for a further 2.5 hrs, then treated with water (100 ml), followed after 0.25 hrs with 10% aqueous $Na_2CO_3$ solution and then extracted with ethyl acetate. The extract was washed with water, 5M HCl acid, then brine, dried ($Na_2SO_4$) and concentrated in vacuo to afford the title compound as a pale yellow solid (61.6 g, 89%).

$^1$H NMR (250 MHz, $CDCl_3$) δ (ppm): 7.54 (d, 1H), 7.48 (d, 1H), 7.30 (dd, 11), 3.82 (t, 2H), 2.58 (t, 2H), 2.40 (s, 3H), 2.16 (quintet, 2H).

DESCRIPTION 47

2'-Methyl-4'-(2-oxopyrrolidin-1-yl)biphenyl-4-carboxylic acid

A stirred mixture of 1-(4-bromo-3-methylphenyl)pyrrolidin-2-one (D46, 50 g, 0.20 mole) and 4-boronobenzoic acid (32 g, 0.20 mole) in 1,2-dimethoxyethane (500 ml) was treated with a solution of $Na_2CO_3$ (94 g, 0.88 mole) in water (500 ml), then de-gassed by bubbling argon through for 0.25 hrs. Tetrakis (triphenylphosphine)palladium (O) (5 g) was added and the mixture heated under reflux for 22 hours, then allowed to cool and concentrated in vacuo to approx. 50% volume. The aqueous residue was diluted with water to approx. 1000 ml, washed with ethyl acetate, then acidified with conc. HCl acid. The precipitate was filtered off, washed with water, dried and recrystallised from ethanol to afford the title compound as a cream solid (30.3 g, 52%).

$^1$H NMR (250 MHz, $d^6$DMSO) δ (ppm): 8.01 (d, 2H), 7.67–7.58 (m, 2H), 7.49 (d, 2H), 7.25 (d, 1H), 3.86 (t, 2H), 2.52 (t, 2H), 2.25 (s, 3H), 2.09 (quintet, 2H).

DESCRIPTION 48

1,2,3,6-Tetrahydro-1,2,6-trimethylpyridine-4-methanol

A stirred solution of 2,6-dimethylpyridine-4-methanol (*Synthetic Comm.* 1989, 19, 317) (10.2 g, 0.07 mol) in acetone (50 ml) and methanol (20 ml) was treated with iodomethane (27.8 ml, 0.45 mol) under argon. After 24 h the precipitate was filtered off, washed with acetone and dried (15.7 g). This solid was dissolved in a mixture of water (80 ml) and ethanol (80 ml) and the stirred solution at 5° C. under argon was treated portionwise over 1.5 hrs with sodium borohydride (3.2 g, 0.085 mole). The reaction mixture was then allowed to warm to room temperature and stirred for 18 hours. The mixture was concentrated in vacuo, then diluted with water, treated with $K_2CO_3$ and extracted with ethyl acetate, then chloroform. The two extracts were combined, dried ($Na_2SO_4$), filtered through kieselguhr, and concentrated in vacuo to yield a brown oil (5.7 g, 66%). This was a cis/trans mixture of the title compound.

$^1$H NMR (250 MHz, $CDCl_3$) δ (ppm): 5.53 and 5.41 (together 1H), 4.00 (s, 2H), 3.43 (d) and 3.15–2.95 (m) and 2.80 (br m) (all together 2H).

DESCRIPTION 49

1-Acetyl-6-bromo-2,3-dihydro-5–1(1,2,3,6-tetrahydro-1,2,6-trimethylpyridin-4-yl)methoxyl-1-indole The title compound was prepared from 1,2,3,6-tetrahydro-1,2,6-trimethylpyridine-4-methanol (D48, mixture of isomers) and 1-acetyl-6-bromo-2,3-dihydro-1H-indol-5-ol (*Tetrahedron* 1973, 29 (8), 1115) following the method of Description 8a in WO 96/19477. The cis and trans 2,6-dimethyl isomers were separated by column chromatography on silica gel eluting with 0–5% methanol/dichloromethane.

cis isomer, 17% yield—$^1$H NMR (250 MHz, CDCl$_3$) δ (ppm): 8.43 (s, 1H), 6.75 (s, 1H), 5.55 (s, 1H), 4.40 (s, 2H), 4.05 (t, 2H), 3.12 (t, 2H), 2.87 (br m, 1H), 2.53–2.35 (m, 1H), 2.30 (s, 3H1), 2.20 (s, 3H), 2.17–2.03 (m, 2H), 1.20 (d, 6H). trans isomer, 10% yield—$^1$H NMR (250 MHz, CDCl$_3$) δ (ppm): 8.44 (s, 1H), 6.73 (s, 1H), 5.65 (br s, 1H), 4.43 (s, 2H), 4.06 (t, 2H), 3.20–3.04 (m, 3H), 2.45–2.30 (m, 1H), 2.35 (s, 3H), 2.20 (s, 3H), 2.03–1.80 (m, 2H), 1.14 (d, 3H), 1.04 (d, 3H).

DESCRIPTION 50 cis-2',6'-dimethyl isomer of 5-Acetyl-2,3,6,7-tetrahydro-1',2',6'-trimethylspiro[furo[2,3-f]indole-3, 4'-piperidine]

The title compound was prepared from the cis 2,6-dimethyl isomer of 1-acetyl-6-bromo-2,3-dihydro-5-[(1,2,3, 6-tetrahydro-1,2,6-trimethylpyridin-4-yl)methoxy]-1H-indole (D49) following the procedure described in Description 8b in WO 96/19477. A 3:1 mixture of two isomers (A:B) around the spirocyclic junction was produced as a yellow solid (88%).

$^1$H NMR (250 MHz, CDCl$_3$) δ (ppm): 8.57 (s, 1H-isomer A), 8.06 (s, 1H-isomer B), 6.64 (s, 1H-isomer A), 6.60 (s, 1H-isomer B), 4.40 (s, 2H-isomer B), 4.15 (s, 2H-isomer A), 4.04 (t, 2H-A and B), 3.13 (t, 2H-A and B), 2.83–2.66 (m, 2H -probably A), 2.40 (s, 3H-isomer A), 2.30 (s, 3H-isomer B), 2.22 (s, 3H-isomer A), 2.20 (s, 3H-isomer B), 1.90–1.40 (m), 1.16 (d, 6H-isomer B), 1.12 (d, 6H-isomer A).

DESCRIPTION 51 cis-2',6'-dimethyl isomer of 2,3,6,7-Tetrahydro-1',2', 6'-trimethylspiro[furo[2,3-f]indole-3t4'-piperidine]

A 3:1 isomeric mixture of the title compound was prepared from the 3:1 isomeric mixture of 5-acetyl-2,3,6,7-tetrahydro-1',2',6'-trimethylspiro[furo[2,3-f]indole-3,4'-piperidine](D50, cis-2',6'-dimethyl isomer) following a similar procedure to Description 8c in WO96/19477.

$^1$H NMR (250 MHz, CDCl$_3$) δ (ppm): 6.90 (s, 1-isomer A), 6.65 (s, 1-isomer A), 6.61 (s, 1H-isomer B), 6.42 (s, 1-isomer B), 4.35 (s, 2H-isomer B), 4.09 (s, 2H-isomer A), 3.54 (t, 2H-isomer A), 3.50 (t, 2H-isomer B), 2.97 (t, 2H-isomer A), 2.95 (t, 2H-isomer B), 2.70–2.54 (m), 2.37 (s, 3H-isomer A), 2.30 (s, 3H-isomer B), 2.18–2.00 (m), 1.90–1.40 (m), 1.17 (d, 6H-isomer B), 1.12 (d, 6H-isomer A).

DESCRIPTION 52

Methyl 2-bromo-5-(2-oxopyrrolidin-1-yl)benzoate

The title compound was prepared from methyl 5-amino-2-bromobenzoate (*J. Med. Chem.* 1970, 13 (3), 567) following a similar procedure to Description 46 as a tan powder (73%).

$^1$H NMR (250 MHz, CDCl$_3$) δ (ppm): 7.95 (s, 1H), 7.8 (d, 1H), 7.61 (d, 1H), 3.92 (s, 3H), 3.86 (t 2H), 2.62 (t, 2H), 2.2 (quintet, 2H).

DESCRIPTION 53

2'-Methoxycarbonyl-4'-(2-oxopyrrolidin-1-yl) biphenyl-4-carboxylic acid

A stirred solution of methyl 2-bromo-5-(2-oxopyrrolidin-1-yl)benzoate (D52, 1.7 g; 5.73 mmol) in DMF (13 ml) was treated with 4-boronobenzoic acid (0.95 g,5.73 mmol) under argon, followed by tetrakis(triphenylphosphine)palladium (O) (104 mg) and triethylamine (2.34 ml, 0.02 mol). After heating for 18 h at 100° C., the reaction mixture was concentrated under reduced pressure and the residue partitioned between 10% aqueous Na$_2$CO$_3$ solution and ethyl acetate. The basic aqueous layer was acidified with 5M HCl acid, precipitating the crude product as a white solid, which was recrystallised from ethanol (137 mg, 7%).

$^1$H NMR (250 MHz, d$^6$ DMSO) δ (ppm): 8.15 (s, 1H), 7.98 (d, 2H), 7.87 (d, 1H), 7.5 (d, 1H), 7.4 (d, 2H), 3.9 (t, 2H), 3.6 (s, 3H), 2.6–2.5 (m, 2H), 2.1 (quintet, 2H).

DESCRIPTION 54

Ethyl 2'-hydroxymethyl-4'-(2-oxopyrrolidin-1-yl) biphenyl-4-carboxylate

Methyl 2'-methyl-4'-(2-oxopyrrolidin-1-yl)biphenyl-4-carboxylate (D4) (5.56 g, 18 mmol), N-bromosuccinimide (3.52 g, 20 mmol) and dibenzoyl peroxide (0.2 g, 0.8 mmol) were stirred at reflux in carbon tetrachloride (250 ml) for 4 h. Further N-bromosuccinimide and dibenzoyl peroxide were then added, and reaction continued for 5 h. The mixture was then cooled, washed with water, dried (Na$_2$SO$_4$) and evaporated to give crude 2'-bromomethyl compound, 8.28 g, as a brown gum. This was stirred at reflux in acetic acid (200 ml) with anhydrous sodium acetate (20 g) for 24 h, cooled, concentrated in vacuo, dissolved in ethyl acetate, washed with 10% Na$_2$CO$_3$, dried (Na$_2$SO$_4$) and evaporated to give crude 2'-acetoxymethyl compound, 4.58 g, as a brown gun. This was stirred in ethanol (100 ml), and treated with NaOH (2.0 g) in water (20 ml) for 5 min. The solution was diluted with ethyl acetate, acidified with 5M HCl/brine, and separated. The organic portion was washed with sat. K$_2$CO$_3$, dried (Na$_2$CO$_3$) and evaporated to give a dark gum. Purification by chromatography on silica, eluting with 0–100% ethyl acetate/dichloromethane, gave the title compound (1.03 g, 17%), containing ca. 10% of the methyl ester.

$^1$H NMR (250 MHz, CDCl$_3$) δ (ppm): 8.09 (d, 2H), 7.80 (d, 1H), 7.66 (dd, 1H), 7.44 (d, 2H), 7.30 (d, 1H), 4.60 (s, 2H), 4.41 (q, 2H), 3.93 (t, 2H), 2.65 (t, 2H), 2.19 (m, 2H), 2.1–2.4 (b, 1H), 1.42 (t, 3H).

DESCRIPTION 55

Ethyl 2'-methoxymethyl-4'-(2-oxopyrrolidin-1-yl) biphenyl-4-carboxylate

Ethyl 2'-hydroxymethyl-4'-(2-oxopyrrolidin-1-yl) biphenyl-4-carboxylate (D54) (0.51 g, 1.5 mmol) was stirred in dry DMF (8 ml) under argon. Sodium hydride (80% dispersion, 0.07 g, 2.3 mmol) was added, and the resulting suspension was stirred for 10 min. Iodomethane (0.19 ml, 3.0 mmol) was added; the mixture was stirred for 30 min, diluted with ethyl acetate, washed with water and brine, dried (Na$_2$SO$_4$) and evaporated to a yellow gum. Chromatography on silica gel, eluting with 0–50% ethyl acetate/dichloromethane, gave the title compound (0.34 g, 64%) as a colourless gum, solidifying on standing. A little methyl ester was also present.

$^1$H NMR (200 MHz, CDCl$_3$) δ (ppm): 8.09 (m, 2H), 7.75 (dd, 1H), 7.69 (d, 1H), 7.44 (d, 2H), 7.30 (d, 1H), 4.41 (q, 2H), 4.32 (s, 2H), 3.93 (t, 2H), 3.34 (s, 3H), 2.64 (t, 2H), 2.19 (quintet, 21), 1.42 (t, 3H).

DESCRIPTION 56

4-Trifluoromethanesulfonyloxy-1-tert-butyl-1,2,3,6-tetrahydropyridine

A stirred solution of diisopropylamine (3.35 ml, 0.025 mol) in dry tetrahydrofuran (70 ml) at −65° C. under argon, was treated with n-butyllithium (13.7 mL; 0.022 mol of a 1.6M sol. in hexanes) and the reaction was stirred at this temperature for 15 minutes. A solution of 1-tert-butylpiperidin-4-one (prepared by the method of Katritzky et al, JCS (B), 1971, 6, 1302–7) (3.1 g; 0.02 mol) in dry tetrahydrofuran (15 mis) was added over 15 minutes, maintaining the temperature at <−60° C. Stirring was continued at this temperature for 2.5 h, then a solution of N-phenyltrifluoromethane sulfonimide (7.82 g; 0.022 mol) in dry tetrahydrofuran was added, and the reaction was allowed to warm to room temperature, and stirred for 1.5 h. The solvents were evaporated under reduced pressure and the residue was purified on a neutral alumina column, eluting with 60–80 petrol ether and diethyl ether, to give the title compound as a yellow oil (2.43 g, 42%).

$^1$H NMR (200 MHz, CDCl$_3$) δ (ppm): 5.74 (m, 1H), 3.25 (q, 2H), 2.77 (t, 2H), 2.43 (br, s, 2H), 1.1 (s, 9H).

DESCRIPTION 57

Methyl 1-tert-butyl-1,2,3,6-tetrahydropyridine-4-carboxylate

A stirred solution of 4-trifluoromethanesulfonyloxy-1-tert-butyl-1,2,3,6-tetrahydropyridine (D56) (2.43 g; 8.5 mmol) in methanol (30 ml) was treated with triethylamine (2.35 ml; 0.017 mol) and triphenylphosphine (0.13 g; 0.289 mmol) and the mixture was purged with carbon monoxide gas for 5 minutes before palladium II acetate (0.055 g; 0.23 mmol) was added. The reaction flask was sealed under a carbon monoxide atmosphere and stirred at room temperature for 72 h. The mixture was filtered through kieselguhr, then evaporated under reduced pressure, and the residue purified by chromatography on silica gel eluting with dichloromethane and methanol to give the title compound (885 mg, 53%).

$^1$H NMR (200 MHz, CDCl$_3$) δ (ppm): 6.95–6.88 (m, 1H), 3.74 (s, 3H), 3.32 (q, 2H), 2.69 (t, 2H), 2.48–2.35 (m, 2H), 1.12 (s, 9H).

DESCRIPTION 58

1-tert-Butyl-1,2,3,6-tetrahydropyridine-4-methanol

A solution of methyl 1-tert-butyl-1,2,3,6-tetrahydropyridine-4-carboxylate (D57) (855 mg; 4.3 mmol) in dry tetrahydrofuran (10 ml) was added to a stirred suspension of lithium aluminium hydride (223 mg; 58 mmol) in dry tetrahydrofuran (20 ml) at 0° C. over 5 minutes. After stirring at 0° C. for 1 h, water (0.22 ml), 10% sodium hydroxide (0.33 ml) and water (0.55 ml) were added, and stirring continued for 30 minutes. The mixture was filtered through kieselguhr, and the filtrate evaporated under reduced pressure to give the title compound as an orange oil (610 mg, 83%).

$^1$H NMR (250 MHz, CDCl$_3$)δ (ppm): 5.65 (br s, 1H), 4.0 (s, 2H), 3.15 (br s, 2H), 2.67 (t, 2H), 2.15 (br s, 3H), 1.1 (s, 9H).

DESCRIPTION 59

1-Acetyl-6-bromo-5-(1-tert-butyl-1,2,3,6-tetrahydropyridine-4-yl)methoxy-2,3-dihydroindole The title compound was prepared from 1-tert-butyl-1,2,3,6-tetrahydropyridine-4-methanol (D58) and 1-acetyl-6-bromo-2,3-dihydroindol-5-ol (*Tetrahedron*, 1973, 29 (8), 1115) using the method outlined in Description 8a in WO 96/19477 (68%).

$^1$H NMR (200 MHz, CDCl$_3$)δ (ppm): 8.42 (s, 1H), 6.75 (s, 1H), 5.82 (br s, 1H), 4.42 (s, 2H), 4.05 (t, 2H), 3.24–3.05 (m, 4H), 2.7 (t, 2H), 2.34–2.22 (m, 2H), 2.2 (s, 3H), 1.12 (s, 9H).

DESCRIPTION 60

5-Acetyl-1'-tert-butyl-2,3,6,7-tetrahydrospiro[furo[2,3-f]indole-3,4'-piperidine]

The title compound was prepared from 1-acetyl-6-bromo-5-(1-tert-butyl-1,2,3,6-tetrahydropyridine-4-yl)methoxy-2,3-dihydroindole (D59) using the method outlined in Description 8b in WO 96/19477 (91%).

$^1$H NMR (250 MHz, CDCl$_3$) δ (ppm): 8.15 (s, 1H), 6.6 (s, 1H), 4.35 (s, 2H), 4.01 (t, 2H), 3.18–2.98 (m, 4H), 2.2 (s, 3H), 2.16–1.95 (m, 4H), 1.8–1.65 (m, 2H), 1.1 (s, 9H).

DESCRIPTION 61

1'-tert-Butyl-2,3,6,7-tetrahydrospiro[furo[2,3-f]indole-3,4'-piperidine]

The title compound was prepared from 5-acetyl-1'-tert-butyl-2,3,6,7-tetrahydrospiro[furo [2,3-f]indole-3,4'-piperidine] (D60) using the method outlined in Description 8c in WO 96/19477 (47%).

$^1$H NMR (200 MHz, CDCl$_3$) δ (ppm): 6.6 (s, 1H), 6.5 (s, 1H), 4.3 (s, 2H), 3.51 (t, 2H), 3.1–2.9 (m, 4H), 2.2–2.04 (m, 2H), 1.99–1.82 (m, 2H), 1.8–1.67 (m, 2H), 1.1 (s, 9H).

DESCRIPTION 62

1-Acetyl-6-aminoindoline

6-Nitroindoline (15.63 g, 0.095 mol) was refluxed for 0.25 h in acetic anhydride (100 ml), cooled, and the precipitate filtered and washed with water, before drying in vacuo. This material (16.6 g, 0.08 mol) was hydrogenated in ethanol (500 ml) over 10% palladium on charcoal (3.4 g of 50% paste in water). The catalyst was removed by filtration and the filtrate was evaporated to leave the title compound as an off-white/cream powder (12.59 g; 89%).

$^1$H NMR (250 MHz, CDCl$_3$) δ (ppm): 7.66 (s, 1H), 6.92 (d, 1H), 6.35 (d, 1H), 4.01 (t, 2H), 3.65 (br s, 2H), 3.05 (t, 2H), 2.2 (s, 3H).

DESCRIPTION 63

1-Acetyl-6-hydroxyindoline

A solution of 1-acetyl-6-aminoindoline (D62, 12 g, 0.068 mol) in concentrated sulfuric acid (9 ml) and water (137 ml) was cooled to 0° C. and diazotised by the dropwise addition of sodium nitrite (4.8 g) in water (34 ml), maintaining the temperature at below 5° C. After 0.5 h, the reaction mixture was added to a boiling stirred solution of copper (II) sulfate (69 g) in water (120 ml). After evolution of nitrogen had ceased, the mixture was cooled, and the precipitate collected by filtration, washed with water, then dried. The compound was purified by column chromatography of its 0-acetyl derivative, then hydrolysed with aqueous NaOH at 20° C. over 18 hrs to afford the title compound as a grey solid (2.6 g, 22%).

$^1$H NMR (250 MHz, d$^6$DMSO) δ (ppm): 9.20 (s, 1H), 7.58 (d, 1H), 6.96 (d, 1H), 6.35 (dd, 1H), 4.04 (t, 2H), 2.98 (t, 2H), 2.12 (s, 3H).

DESCRIPTION 64

1-Acetyl-5-bromo-6-hydroxyindoline

A stirred suspension of finely powdered 1-acetyl-6-hydroxyindoline (D63, 2.4 g, 0.013 mole) in a mixture of DMF (25 ml) and glacial acetic acid (125 ml) at 15° C. was treated portionwise over 5 minutes with N-bromosuccinimide (2.65 g, 0.015 mole). The reaction mixture changed from yellow to grey-green in colour. The mixture was stirred at 1 5–20° C. for 45 minutes, then cooled to 5° C. and the solid filtered off, washed with acetic acid and dried to give the title compound as a grey solid (2.45 g, 71%).

$^1$H NMR (250 MHz, d$^6$DMSO) δ (ppm): 7.82 (s, 1H), 7.26 (s, 1H), 4.05 (t, 2H), 3.00 (t, 2H), 2.12 (s, 3H).

DESCRIPTION 65

1-Acetyl-5-bromo-6-[(1-methyl-1,2,5,6-tetrahydropyridine-4-yl)methoxy]indoline

The title compound was prepared from 1-acetyl-5-bromo-6-hydroxyindoline (D64) and 1-methyl-1,2,5,6-tetrahydropyridine-4-methanol (*J. Med. Chem.*, 1988, 31, 545) using the procedure of Description 8a in WO96/19477. The product was purified by acid/base extraction, then used in the next step.

1H NMR (250 MHz, CDCl$_3$) δ (ppm): 7.96 (s, 1H), 7.27 (s, 1H), 5.84 (m, 1H), 4.50 (s, 2H), 4.05 (t, 2H), 3.10 (t, 2H), 3.03–2.95 (m, 2H), 2.58 (t, 2H), 2.35 (s, 3H), 2.35–2.25 (m, 2H), 2.20 (s, 3H).

DESCRIPTION 66

7-Acetyl-1'-methyl-2,3,5,6-tetrahydrospiro[furo[3,2-f]indole-3,4'-piperidine]

The title compound was prepared from 1-acetyl-5-bromo-6-[(1-methyl-1,2,5,6-tetrahydropyridine-4-yl)methoxy]indoline (D65) using a similar procedure to Description 8b in WO96/19477, but with toluene at 80° C. in place of refluxing benzene. The product was obtained from the acid/base purification as a beige solid (94%).

$^1$H NMR (250 MHz, CDCl$_3$) δ (ppm): 7.75 (s, 1H), 6.85 (s, 1H), 4.37 (s, 2H), 4.05 (t, 2H), 3.10 (t, 2H), 2.95–2.75 (m, 2H), 2.30 (s, 3H), 2.20 (s, 3H), 2.05–1.85 (m, 4H), 1.80–1.65 (m, 2H).

DESCRIPTION 67

1'-Methyl-2,3,5,6-tetrahydrospiro[furo[3,2-f]indole-3,4'-piperidine]

The title compound was prepared from 7-acetyl-1'-methyl-2,3,5,6-tetrahydrospiro[furo[3,2-f]indole-3,4'-piperidine] (D66) using the procedure of Description 8c in WO96/19477. The product was recrystallised from ethyl acetate/60–80 petrol (44%).

$^1$H NMR (250 MHz, CDCl$_3$) δ (ppm): 6.83 (s, 1H), 6.05 (s, 1H), 4.32 (s, 2H), 3.7 (br s, 1H), 3.55 (t, 2H), 2.93 (t, 2H), 2.90–2.75 (m, 2H), 2.30 (s, 3H), 2.05–1.85 (m, 4H), 1.80–1.65 (m, 2H).

DESCRIPTION 68

2,3-Dihydro-1'-methylspiro[furo[3,2-f]indole-3,4'-piperidine] 2,3-Dihydro-1'-methylspiro[furo[3,2-f]indole-3,4'-piperidine]

A stirred solution of 1'-methyl-2,3,5,6-tetrahydrospiro[furo[3,2-f]indole-3,4'-piperidine] (D67, 1.0 g, 4.1 mmole) in dichloromethane (70 ml) at room temp. under argon was treated with manganese dioxide (0.68 g, 8.2 mmole). The mixture was stirred for 18 hours, then additional manganese dioxide was added (0.30 g, 2.4 mnmole). The mixture was stirred for an additional 24 hours, then filtered through a pad of kieselguhr and the filtrate concentrated under vacuum. The two components present were separated by chromatography on neutral alumina. Elution with ether gave the title compound as a white solid (0.41 g, 41%), further elution with ethyl acetate gave the second component.

$^1$H NMR (200 MHz, CDCl$_3$) δ (ppm): 8.10 (br s, 1H), 7.32 (s, 11), 7.10–7.04 (m, 1H), 6.78 (s, 1H), 6.50–6.43 (m, 1H), 4.40 (s, 2H), 2.90–2.80 (m, 2H), 2.35 (s, 3H), 2.20–1.95 (m, 4H), 1.90–1.70 (m, 2H).

Example 1

5-[2'-Methyl-4'-(2-oxo-1-pyrrolidinyl)biphenyl-4-carbonyl]-1'-methyl-2,3,6,7-tetrahydrospiro[furo]indole-3,4'-peperidine]

1'-Methyl-2,3,6,7-tetrahydrospiro[furo[2,3-f]indole-3,4'-piperidine] (D7) 0.200 g, 0.82 mmol) was stirred under argon in toluene (5 ml) as trimethylaluminium (2M in toluene, 0.45 ml, 0.90 mmol) was added. The clear solution was stirred for 15 min, when methyl 2'-methyl-4'-(2-oxo-1-pyrrolidinyl)biphenyl-4-carboxylate (D4, 0.240 g, 0.78 mmol) was added. The mixture was stirred at 80° C. under argon for 6 h, cooled and poured into a stirred slurry of silica gel (10 g) in dichloromethane. The silica gel was washed with 20% MeOH/dichloromethane, and the organics were evaporated to give the crude product as an oil. Chromatography on silica gel, eluting with 0–10% MeOH/dichloromethane, gave the title compound (0.263 g, 61%) as a light green gum. This was converted to the hydrochloride salt by dissolution in dichloromethane, addition of HCl in ether (1M solution), and precipitation with ether.

$^1$H NMR (250 MHz, d$^6$DMSO) δ (ppm): 10.60 (bs, 1H), 7.93 (bs, 1H), 7.6 (m, 4H), 7.44 (d, 2H), 7.27 (d, 1H), 6.77 (s, 1H), 4.52 (s, 2H), 4.06 (t, 2H), 3.87 (t, 2H) 3.4 (m, 2H), 2.95–3.2 (m, 4H), 2.77 (s, 3H), 2.55 (m, 2H), 2.29 (s, 3H), 2.0–2.25 (m, 4H), 1.88 (d, 2H).

Example 2

1'-Methyl-5-[2'-methyl-4'-(2-oxo-1-piperidinyl)biphenyl-4-carbonyl]-2,3,6,7-tetrahydrospiro[furo[2,3-f]indole-3,4'-piperidine]

Similar procedure to E1, from D7 and D10.

$^1$H NMR (250 MHz, d$^6$DMSO) δ (ppm): 10.38 (bs, 1H), 7.94 (bs, 1H), 7.65 (d, 2H), 7.47 (d, 2H), 7.15–7.30 (m, 3H), 6.77 (s, 1H), 4.50 (s, 2H), 4.06 (t, 2H), 3.63 (m, 2H), 3.4 (m, 2H), 3.0–3.2 (m, 4H), 2.77 (s, 3H), 2.40 (m, 2H), 2.26 (s, 3H), 2.2 (m, 2H), 1.85 (m, 6H).

Example 3

5-[4'-(4,5-Dihydro-2-oxooxazol-3-yl)-2'-methylbiphenyl-4-carbonyl]-1'-methyl-2,3,6,7-tetrahydrospiro[furo[2,3-f]indole-3,4'-piperidine]

Similar procedure to E1, from D7 and D11.

$^1$H NMR (250 MHz, d$^6$DMSO) δ (ppm): 10.62 (bs, 1H), 7.93 (bs, 1H), 7.63 (d, 2H), 7.5 (m, 2H), 7.45 (d, 2H), 7.29 (d, 1H), 6.77 (s, 1H), 4.51 (s, 2H), 4.47 (t, 2H), 4.1 (m, 4H), 3.4 (m, 2H), 2.95–3.2 (m, 4H), 2.76 (s, 3H), 2.30 (s, 3H), 2.2 (m, 2H), 1.87 (d, 2H).

Example 4

5-(4'-Acetamido-2'-methylbiphenyl-4-carbonyl)-1'-methyl-2,3,6,7-tetrahydrospiro[furo[2,3-f]indole-3,4'-piperidine]

The title compound was prepared from 4'-acetamido-2'-methylbiphenyl-4-carboxylic acid (D13) and 1'-methyl-2,3, 6,7-tetrahydrospiro[furo[2,3-f]indole-3,4'-piperidinel (D7) using oxalyl chloride to give the title compound as a yellow oil (43%). This was converted to its oxalate salt which crystallised as a white solid from acetone.

$^1$H NMR (oxalate salt) (400 MHz, d$^6$DMSO) δ (ppm): 10.00 (s, 1H), 7.95 (br s, 1H), 7.62 (d, 2H), 7.55–7.50 (m, 2H), 7.43 (d, 2H), 7.19 (d, 1H), 6.77 (s, 1H), 4.50 (s, 2H), 4.05 (t, 2H), 3.40 (br, 2H), 3.08–2.93 (m, 4H), 2.75 (br s, 3H), 2.25 (s, 3H), 2.17–2.00)m, 2H), 2.06 (s, 3H), 1.94–1.80 (m, 2H).

Example 5

1'-Methyl-5-[2'-methyl-4'-(2-thioxo-1-pyrrolidinyl)biphenyl-4-carbonyll-2,3,6,7-tetrahydrospiro[furo[2,3-f]indole-3,4'-piperidine]

The title compound was prepared by a similar procedure to E1, from D7 and D14. The crude product was chromatographed on silica gel and eluted with 30% MeOH/DCM to afford a pale yellow solid (90 mg). This was converted to its hydrochloride salt and crystallised from acetone to afford a white solid.

$^1$H NMR (free base) (250 MHz, CDCl$_3$) δ (ppm): 8.16 (bs, 1H—low integration), 7.61 (d, 2H), 7.47–7.23 (m, 5H), 6.68 (s, 1H), 4.40 (bs, 2H), 4.24–3.98 (m, 4H), 3.28 (t, 2H), 3.07 (t, 2H), 2.97–2.76 (m, 2H), 2.32 (s, 3H), 2.43–1.46 (m, 1H).

Example 6

5-[4'-(1,1-Dioxo-2,3,4,5-tetrahydroisothiazol-2-yl)-2'-methylbiphenyl-4-carbonyl]-1'-methyl-2,3,6,7-tetrahydrospiro[furo[2,3-f]indole-3,4'-piperidine]

This was prepared from methyl 4'-(1,1-dioxo-2,3,4,5-tetrahydroisothiazol-2-yl)-2'-methylbiphenyl-4-carboxylate (D16), following the procedure of Example 1. This gave the title compound as a white solid (31%). This was converted to its hydrochloride salt.

$^1$H NMR (HCl salt) (250 MHz, d$^6$DMSO) δ (ppm): 10.4 (b, 1H), 7.95 (b, 1H), 7.64 (d, 2H), 7.44 (d, 2H), 7.28 (d, 1H), 7.16 (m, 2H), 6.78 (s, 1H), 4.51 (s, 2H), 4.05 (t, 2H), 3.78 (t, 2H), 3.54 (t, 2H), 3.4 (m, 2H), 3.02 (m, 4H), 2.77 (s, 3H), 2.45 (m, 2H), 2.29 (s, 3H), 25 2.2 (m, 211), 1.9 (d, 2H).

Example 7

5-[4'-(4,5-Dihydro-2-oxoimidazol-1-yl)-2'-methylbiphenyl-4-carbonyl]-1'-methyl-2,3,6,7-tetrahydrospirolfuro[2,3-f]indole-3,4'-piperidine]

This was prepared from methyl 4'-(4,5-dihydro-2-oxoimidazol-1-yl)-2'-methylbiphenyl-4-carboxylate (D18), following the procedure of Example 1. This gave the title compound as a white solid (23%).

$^1$H NMR (250 Mz, CDCl$_{13}$/d$^6$DMSO) δ (ppm): 7.98 (b, 11H), 7.58 (d, 2H), 7.47 (m, 2H), 7.40 (d, 2H), 7.16 (d, 1H), 6.92 (s, 1H), 6.66 (s, 1H), 4.37 (s, 2H), 4.10 (t, 2H), 3.91 (t, 2H), 3.48 (t, 2H), 3.05 (t, 2H), 2.8 (m, 2H), 2.30 (s, 3H), 2.25 (s, 3H), 1.95 (m, 4H), 1.7 (m, 2H).

Example 8

5-[4'-(4,5-Dihydro-3-methyl-2-oxoimidazol-1-yl)-2'-methylbiphenyl-4-carbonyl]-9'-methyl-2,3,6,7-tetrahydrospiro[furol2,3-f]indole-3,4'-piperidine]

This was prepared from methyl 4'-(4,5-dihydro-3-methyl-2-oxoimidazol-1-yl)-2'-methylbiphenyl-4-carboxylate (D19), following the procedure of Example 1. This gave the title compound as a colourless gum (53%). This was converted to its hydrochloride salt.

$^1$H NMR (HCl salt) (200 MHz, d$^6$DMSO) δ (ppm): 10.58 (b, 1H), 7.93 (b, 1H), 7.62 (d, 2H), 7.4–7.6 (m, 4H), 7.21 (d, 1H), 6.77 (s, 1H), 4.51 (s, 2H), 4.05 (t, 2H), 3.82 (t, 2H), 3.3–3.55 (m, 4H), 2.95–3.2 (m, 4H), 2.78 (s, 6H), 2.28 (s, 3H), 2.1–2.3 (m, 2H), 1.88 (d, 2H).

Example 9

1'-Metbyl-5–12'-methyl-4'-(3-methyl-2-oxopyrrolidin-1-yl)biphenyl-4-carbonyl]-2,3,6,7-tetrahydrospiro[furo[2,3-f]indole-3,4'-piperidine]

The title compound was prepared from methyl 2'-methyl-4'-(3-methyl-2-oxopyrrolidin-1-yl)biphenyl-4-carboxylate (D22) and 1'-methyl-2,3,6,7-tetrahydrospiro[furo[2,3-f]indole-3,4'-piperidine] (D7) following the method of Example 1. The pale yellow oil (64%) was converted to its hydrochloride salt, crystallising from acetone.

$^1$H NMR (free base) (250 MHz, CDCl$_3$) δ (ppm): 8.15 (br s, 1H), 7.65–7.55 (m, 3H), 7.51 (dd, 1H), 7.37 (d, 2H), 7.25 (d, 1H), 6.67 (s, 1H), 4.39 (br s, 2H), 4.20–4.00 (br m, 2H), 3.88–3.77 (m, 2H), 3.06 (t, 2H), 2.96–2.75 (br m, 2H), 2.80–2.62 (m, 1H), 2.50–2.25 (m, 1H), 2.31 (s, 6H), 2.20–1.60 (m, 7H), 1.32 (d, 3H).

Example 10

5-4'-(3,3-Dimethyl-2-oxopyrrolidin-1-y[)-2'-methylbiphenyl-4-carbonyl]-1'-methyl-2,3,6,7-tetrahydrospiro[furo[2,3-f]indole-3,4'-piperidine]

The title compound was prepared from methyl 4'-(3,3-dimethyl-2-oxopyrrolidin-1-yl)-2'-methylbiphenyl-4-carboxylate (D25) and 1'-methyl-2,3,6,7-tetrahydrospiro[furo-[2,3-f]indole-3,4'-piperidine] (D7) following the method of Example 1. The pale yellow oil (73%) was converted to its hydrochloride salt, crystallising from acetone.

$^1$H NMR (free base) (250 MHz, CDCl$_3$) δ (ppm): 8.15 (br s, 1H—low integration), 7.67 (d, 1H), 7.60 (d, 2H), 7.53 (dd, 1H), 7.37 (d, 2H), 7.25 (d, 1H), 6.67 (s, 1H), 4.40 (br s, 2H), 4.20–4.03 (br m, 2H), 3.80 (t, 2H), 3.07 (t, 2H), 2.95–2.75 (br, 2H), 2.30 (s, 6H), 2.15–1.60 (m, 8H), 1.26 (s, 6H).

Example 11

5-[4'-(2,3-Dihydro-1-oxoisoindol-2-yl)-2'-methylbipheny]4-carbonyl]-1'-methyl-2,3,6,7-tetrahydrospiro[furo [2,3-f]indole-3,4'-piperidine]

The title compound was prepared from methyl 4'-(2,3-dihydro-1-oxoisoindol-2-yl)-2'-methylbiphenyl-4-carboxylate (D28) and 1'-methyl-2,3,6,7-tetrahydrospiro[furo-2,3-f]indole-3,4'-piperidine] (D7) following the method of Example 1. The oil (49%) was converted to its hydrochloride salt, crystallising from dichloromethane.

$^1$H NMR (free base) (250 MHz, CDCl$_3$) δ (ppm): 8.15 (br s, 1H), 7.95 (d, 1H), 7.82 (d, 1H), 7.78 (dd, 1H), 7.68–7.48 (m, 5H), 7.41 (d, 2H), 7.31 (d, 1H), 6.67 (s, 1H), 4.90 (s, 2H), 4.40 (br s, 2H), 4.12 (br, 2H), 3.07 (t, 2H), 2.95–2.70 (br m, 2H), 2.36 (s, 3H), 2.30 (s, 3H), 2.20–1.50 (m, 6H).

Example 12

5-[2,3'-Dimethyl-4'-(2-oxopyrrolidin-1-yl)biphenyl-4-carbonyl-1'-methyl-2,3,6,7-tetrahydrospiro[furo[2,3-f]indole-3,4'-piperidine]

The title compound was prepared from methyl 2,3'-dimethyl-4'-(2-oxopyrrolidin-1-yl)biphenyl-4-carboxylate (D32) and 1'-methyl-2,3,6,7-tetrahydrospiro[filro[2,3-f]indole-3,4'-piperidine] (D7) following the method of Example 1. This was obtained as a yellow oil (77%), which was converted to its hydrochloride salt, crystallising from acetone.

$^1$H NMR (free base) (250 MHz, CDCl$_3$) δ (ppm): 8.15 (br s, 1H—low integration), 7.45 (s, 1H), 7.38 (d, 1H), 7.30–7.16 (m, 4H), 6.66 (s, 1H), 4.40 (br s, 2H), 4.20–4.00 (m, 2H), 3.80 (t, 2H), 3.05 (t, 2H), 2.98–2.75 (m, 2H), 2.63 (t, 2H), 2.48–2.18 (m, 11H), 2.15–1.90 (m, 4H), 1.85–1.55 (m, 2H).

Example 13

1'-Methyl-5-[4'-(2-oxo-1-pyrrolidinyl)-2'-trifluoromethylbiphenyl-4-carbonyl]-2,3,6,7-tetrahydrospiro[furo[2,3-f]indole-3,4'-piperidine]

The title compound was prepared from D36 and D7 following a similar procedure to E1, as a white solid (40%).

$^1$H NMR (250 MHz, CDCl$_3$) δ (ppm): 8.16 (brs, 1H—low integration), 8.03–7.87 (m, 2H), 7.58 (d, 2H), 7.44–7.30 (m, 3H), 6.68 (s, 1H), 4.39 (br s, 2H), 4.22–3.99 (br, 2H), 3.95 (t, 2H), 3.07 (t, 2H), 3.02–2.77 (br, 2H), 2.68 (t, 2H), 2.56–1.44 (m, 11H).

Example 14

5-2'-Chloro-4'-(2-oxo-1-pyrrolidinyl)biphenyl-4-carbonyl]-1'-methyl-2,3,6,7-tetrahydrospiro[furo[2,3-f]indole-3,4'-piperidine]

The title compound was prepared from methyl 2'-chloro-4'-(2-oxo-1-pyrrolidinyl)biphenyl-4-carboxylate (D40) and 1'-methyl-2,3,6,7-tetrahydrospiro[furo [2,3-f]indole-3,4'-piperidine] (1)7) following a similar procedure to that described in Example 1. The hydrochloride salt was prepared and recrystallised from acetone to afford a white solid (83%).

$^1$H NMR (free base) (200 MHz, CDCl$_3$) δ (ppm): 8.15 (brs, 1H—low integration), 7.80 (d, 1H), 7.73–7.45 (m, 5H), 7.36 (d, 1H), 6.67 (s, 1H), 4.56–3.98 (br, 4H), 3.90 (t, 2H), 3.07 (t, 2H), 2.97–2.77 (br, 2H), 2.67 (t, 2H), 2.49–1.39 (m, 11H).

Example 15

5-[4-(1-Acetyl-1,2,3,4-tetrabydroquinolin-6-yl)-3-methylbenzoyl]-1'-methyl-2,3,6,7-tetrahydrospirolfuro[2,3-nindole-3,4'-piperidine]

4-(1-Acetyl-1,2,3,4-tetrahydroquinolin-6-yl)-3-methylbenzoic acid (D42, 386 mg, 1.25 mmol) was dissolved in dichloromethane (6 ml) and treated with oxalyl chloride (0.16 ml, 1.88 mmol) and 1 drop of DMF. The mixture was stirred for 0.5 hrs then the excess oxalyl chloride was evaporated using toluene (20 ml). The resultant acid chloride was dissolved in dichloromethane (5 ml) and THF (6 ml) and added to a solution of 1'-methyl-2,3,6,7-tetrahydrospiro[furo[2,3-f]indole-3,4'-piperidine) (D7) (305 mg, 1.25 mmol) and triethylamine (0.35 ml, 2.50 mmol) in THF (8 ml) at 5° C. under argon. The reaction mixture was stirred at room temp. under argon for 2.5 hrs, then concentrated in vacuo, washed with water, treated with 10% aqueous Na$_2$CO$_3$ solution, extracted with DCM and dried (Na$_2$SO$_4$). The filtrate was evaporated to leave a dark orange solid which was purified by chromatography on silica gel, eluting with 0–5% MeOH/DCM to afford the title compound as a yellow foam (95 mg, 14%). The hydrochloride salt of the title compound was isolated as a yellow solid.

$^1$H NMR (HCl salt) (400 MHz, d$^6$DMSO) δ (ppm): 7.93 (brs, 1H—low integration), 7.59–7.39 (m, 3H), 7.30 (d, 1H), 7.26–7.13 (m, 2H), 6.77 (s, 1H), 4.50 (s, 2H), 4.05 (t, 2H), 3.73 (t, 2H), 3.19–2.68 (m, 11H), 2.31 (s, 3H), 2.21 (s, 3H), 2.11–1.76 (m, 6H).

Example 16

5-4-(1-Acetyl-2,3-dihydroindol-5-yl)-3-methylbenzoyl]-1'-methyl-2,3,6,7-tetrahydrospiro[furo[2,3-f]indole-3,4'-piperidine]

The title compound was prepared from 4-(1-acetyl-2,3-dihydroindol-5-yl)-3-methylbenzoic acid (D43, 248 mg, 0.841 mmol) using a similar procedure to that described in Example 15. The hydrochloride salt was isolated as an off-white solid.

$^1$H NMR (free base) (250 MHz, CDCl$_3$) δ (ppm): 8.26 (d, 1H), 8.16 (br s, 1H—low integration), 7.44 (s, 1H), 7.39 (d, 1H), 7.32–7.04 (m, 3H), 6.67 (s, 1H), 4.49–4.28 (br, 2H), 4.21–3.99 (m, 4H), 3.27 (t, 2H), 3.07 (t, 2H), 3.00–2.75 (m, 2H), 2.36 (br s, 3H), 2.31 (s, 3H), 2.28 (s, 3H), 2.21–1.43 (m, 6H).

Example 17

1'-Methyl-5-(2'-methyl-4'-(2-oxo-1-pyrazin-1-yl)biphenyl-4-carbonyl)-2,3,6,7-tetrahydrospiro[furo[2,3-f]indole-3,4'-piperidine]

The title compound was prepared from 2'-methyl-4'-(2-oxo-1H-pyrazin-1-yl)biphenyl-4-carboxylic acid (D45, 250 mg; 0.817 mmol) and 1'-methyl-2,3,6,7-tetrahydrospiro[furo[2,3-f]indole-3,4'-piperidine] (D7, 200 mg; 0.817 mmol) following the procedure outlined in Example 15, as a lemon powder (48 mg, 10%). This was converted to its hydrochloride salt.

$^1$H NMR (free base) (200 MHz, CDCl$_3$) δ (ppm): 8.29 (s, 1H), 8.12 (br s, 1H), 7.61 (d, 2H), 7.5–7.15 (m, 7H), 6.65 (s, 1H), 4.4 (s, 2H), 4.2–3.97 (m, 2H), 3.06 (t, 2H), 2.95–2.72 (m, 2H), 2.3 (s, 6H), 2.2–1.5 (m, 6H).

Example 18

5-[2'-methyl-4'-(2-oxopyrrolidin-1-yl)biphenyl-4-carbonyl]-2,3,6,7-tetrahydrospiro[furo[2,3-f]indole-3,4'-piperidine]

A solution of 5-[2'-methyl-4'-(2-oxo-1-pyrrolidinyl)biphenyl-4-carbonyl]-1'-methyl-2,3,6,7-tetrahydrospiro [furo[2,3-f]indole-3,4'-piperidine (E1, 1.65 g, 3.17 mmol), in 1,2-dichloroethane (40 ml) was treated with diisopropylethylamine (1 ml) and 1-chloroethyl chloroformate (0.62 ml) under argon. After stirring at room temperature for 20 h, the solvents were evaporated under reduced pressure and the residue refluxed in methanol (100 ml) for 1 h. The solution was evaporated under reduced pressure, and the residue partitioned between 10% Na$_2$CO$_3$ and dichloromethane. The organic phase was dried (Na$_2$SO$_4$) and the solvent evaporated under reduced pressure, to leave the title compound as an off-white powder (1.04 g, 65%).

$^1$H NMR (250 MHz, CDCl$_3$) δ (ppm): 8.12 (br s, 1H), 7.64–7.44 (m, 4H), 7.38 (d, 2H) 7.25 (d, 1H), 6.65 (s, 1H), 4.43 (br s, 2H), 4.25–4.0 (m, 2H), 3.9 (t, 2H), 3.2–2.95 (m, 4H), 2.79–2.53 (m, 4H), 2.3 (s, 3H), 2.26–2.1 (m, 2H), 2.03–1.62 (m, 4H). (NH proton not observed).

Example 19

1'-Ethyl-5–12'-methyl-4'-(2-oxopyrrolidin-1-yl)biphenyl-4-carbonyl]-2,3,6,7-tetrahydrospiro[furo[2,3-f]indole-3,4'-piperidine]

A stirred solution of 5-[2'-methyl-4'-(2-oxopyrrolidin-1-yl)biphenyl-4-carbonyl]-2,3,6,7-tetrahydrospiro[furo[2,3-f]

indole-3,4'-piperidine] (E18, 250 mg, 0.49 mmole) in ethanol (12 ml) was treated with anhydrous potassium carbonate (270 mg, 2.0 mmole) and iodoethane (0.08 ml, 1.0 mmole). The mixture was heated under reflux for 6 h, then additional iodoethane (0.04 ml) was added and reflux continued for a further 3 h. The reaction mixture was allowed to cool, filtered and the filtrate concentrated in vacuo and the residue chromatographed on silica gel eluting with 0–4% methanol/chloroform. The title compound was obtained as a pale yellow oil (150 mg, 57%). This was converted to its hydrochloride salt and crystallised from acetone.

$^1$H NMR (free base) (250 MHz, CDCl$_3$) δ (ppm): 8.16 (br s, 1H—low integration), 7.63–7.50 (m, 3H), 7.48 (dd, 1H), 7.38 (d, 2H), 7.23 (d, 1H), 6.65 (s, 1H), 4.38 (br s, 2H), 4.10 (br, 2H), 3.90 (t, 2H), 3.05 (t, 2H), 2.95 (br, 2H), 2.62 (t, 2H), 2.55–2.35 (m, 2H), 2.30 (s, 3H), 2.26–1.60 (m, 10H), 1.10 (br t, 3H).

Example 20

5-[2'-Methyl-4'-(2-oxopyrrolidin-1-yl)biphenyl-4-carbonyl]-1'-n-propyl-2,3,6,7-tetrahydrospiro[furo[2,3-f]indole-3,4'-piperidine]

The title compound was prepared from 5-[2'-methyl-4'-(2-oxopyrrolidin-1-yl)biphenyl-4-carbonyl]-2,3,6,7-tetrahydrospiro[furo[2,3-f]indole-3,4'-piperidine] (E18) and 1-bromopropane using a similar procedure to Example 19, as a colourless oil (78%). This was converted to its hydrochloride salt and crystallised from acetone.

$^1$H NMR (free base) (250 MHz, CDCl$_3$) δ (ppm): 8.16 (br s, 1H—low integration), 7.65–7.53 (m, 3H), 7.50 (dd, 1H), 7.38 (d, 2H), 7.25 (d, 1H), 6.67 (s, 1H), 4.40 (br s, 2H), 4.20–4.00 (m, 2H), 3.91 (t, 2H), 3.07 (t, 2H), 3.05–3.20 (m, 2H), 2.64 (t, 2H), 2.30 (s, 3H), 2.35–1.90 (m, 6H), 1.87–1.43 (m, 6H), 0.90 (t, 3H).

Example 21

1'-Isopropyl-5-[2'-methyl-4'-(2-oxopyrrolidin-1-yl)biphenyl-4-carbonyl]-2,3,6,7-tetrahydrospiro[furo[2,3-f]indole-3,4'-piperidine]

The title compound was prepared from 5-[2'-methyl-4'-(2-oxopyrrolidin-1-yl)biphenyl-4-carbonyl]-2,3,6,7-tetrahydrospiro[firo[2,3-f]indole-3,4'-piperidine] (E18) and 2-bromopropane using a similar procedure to Example 19, as a colourless oil (11%). This was converted to its hydrochloride salt and crystallised from acetone.

$^1$H NMR (free base) (250 MHz, CDCl$_3$) δ (ppm): 8.20 (br s, 1H—low integration), 7.64–7.53 (m, 3H), 7.49 (dd, 1H), 7.38 (d, 2H), 7.25 (d, 1H), 6.67 (s, 1H), 4.38 (br s, 2H), 4.20–4.00 (br, 2H), 3.90 (t, 2H), 3.05 (t, 2H), 3.00–2.65 (m, 3H), 2.63 (t, 2H), 2.30 (s, 3H), 2.30–1.60 (m, 8H), 1.05 (br d, 6H).

Example 22

1'-n-Butyl-5-[2'-methyl-4'-(2-oxopyrrolidin-1-yl)biphenyl-4-carbonyl]-2,3,6,7-tetrahydrospiro[furo[2,3-f]indole-3,4'-piperidine]

The title compound was prepared from 5-[2'-methyl-4'-(2-oxopyrrolidin-1-yl)biphenyl-4-carbonyl]-2,3,6,7-tetrahydrospiro[furo[2,3-f]indole-3,4'-piperidine] (E18) and 1-bromobutane using a similar procedure to Example 19, as a yellow oil (55%). This was converted to its hydrochloride salt and crystallised from acetone as a white solid.

$^1$H NMR (free base) (250 MHz, CDCl$_3$) δ (ppm): 8.17 (br s, 1H—low integration), 7.64–7.53 (m, 3H), 7.49 (dd, 1H), 7.37 (d, 2H), 7.24 (d, 1H), 6.66 (s, 1H), 4.40 (br s, 2H), 4.10 (br m, 2H), 3.90 (t, 2H), 3.07 (t, 2H), 2.95 (br m, 2H), 2.63 (t, 2H), 2.40–1.25 (m, 14H), 2.30 (s, 3H), 0.93 (t, 3H).

Example 23

1'-Cyclopropylmethyl-5-[2'-methyl-4'-(2-oxopyrrolidin-1-yl)biphenyl-4-carbonyl]-2,3,6,7-tetrahydrospiro [furo[2,3-f]indole-3,4'-piperidine]

The title compound was prepared from 5-[2'-methyl-4'-(2-oxopyrrolidin-1-yl)biphenyl-4-carbonyl]-2,3,6,7-tetrahydrospiro[furo[2,3-f]indole-3,4'-piperidine] (E18) and cyclopropylmethyl bromide using a similar procedure to Example 19, as a cream foam (52%). This was converted to the hydrochloride salt, isolated as a white powder.

$^1$H NMR (free base) (200 MHz, CDCl$_3$) δ (ppm): 8.15 (br s, 1H), 7.65–7.15 (m, 7H), 6.65 (s, 1H), 4.38 (s, 2H), 4.2–4.0 (m, 2H), 3.9 (t, 2H), 3.05 (t, 4H), 2.63 (t, 2H), 2.4–1.93 (m, 1 1H), 1.88–1.57 (m, 2H), 0.9 (br s, 1H), 0.6–0.045 (m, 2H), 0.19–0.05 (m, 2H).

Example 24

1'-Allyl-5-[2'-methyl-4'-(2-oxopyrrolidin-1-yl)biphenyl-4-carbonyl]-2,3,6,7-tetrahydrospiro[furo[2,3-f]indole-3,4'-piperidine]

This was prepared from 5-[2'-methyl-4'-(2-oxopyrrolidin-1-yl)biphenyl-4-carbonyl]-2,3,6,7-tetrahydrospiro[furo[2,3-f]indole-3,4'-piperidine] (E18) and allyl bromide using a similar procedure to Example 19, except that DMF was used as solvent in place of ethanol. This gave the title compound as a white foam (11%) which was converted to its hydrochloride salt, crystallising from acetone as a white solid.

$^1$H NMR (free base) (250 MHz, CDCl$_3$) δ (ppm): 8.16 (br s, 1H—low integration), 7.65–7.53 (m, 3H), 7.48 (dd, 1H), 7.35 (d, 2H), 6.66 (s, 1H), 6.00–5.80 (m, 1H), 5.28–5.10 (m, 2H), 4.38 (br s, 2H), 4.10 (m, 2H), 3.90 t, 2H), 3.15–2.85 (m, 6H), 2.30 (s, 3H), 2.20 (quintet, 2H), 2.20–1.50 (m, 6H).

Example 25

1'-Cyclopentyl-5-[2'-methyl-4'-(2-oxopyrrolidin-1-yl)biphenyl-4carbonyl]-2,3,6,7-tetrahydrospiro[furo[2,3-f]indole-3,4'-piperidine]

The title compound was prepared from 5-[2'-methyl-4'-(2-oxopyrrolidin-1-yl)biphenyl-4-carbonyl]-2,3,6,7-tetrahydrospiro[furo[2,3-f]indole-3,4'-piperidine] (E18) and cyclopentyl bromide using a similar procedure to Example 19, as a white powder (22%).

$^1$H NMR (250 MHz, CDCl$_3$) δ (ppm): 8.19 (br s, 1H—low integration), 7.61–7.53 (m, 3H), 7.49 (d, 1H), 7.37 (d, 2H), 7.24 (d, 1H), 6.67 (s, 1H), 4.39 (s, 2H), 4.10 (br m, 2H), 3.92 (t, 2H), 3.07 (m, 4H), 2.65 (t, 2H), 2.70–2.40 (m, 1H), 2.31 (s, 3H), 2.20 (quintet, 2H), 2.12–1.32 (m, 14H).

Example 26

2,3,5,6,7,8-Hexahydro-1'-methyl-5-[2'-methyl-4'-(2-oxopyrrolidin-1-yl)biphenyl-4-carbonyl]spiro[furo [2,3-g]quinoline-3,4'-piperidine]

The title compound was prepared from 2'-methyl-4'-(2-oxopyrrolidin-1-yl)biphenyl-4-carboxylic acid (D47) and 2,3,5,6,7,8-hexahydro-1'-methylspiro[furo[2,3-g]quinoline-3,4'-20 piperidine] (Description 10 in WO96/19477) following a similar procedure to Example 15.

¹H NMR (250 MHz, CDCl₃) δ (ppm): 7.49 (d, 1H), 7.46 (dd, 1H), 7.31 (d, 2H), 7.18 (d, 2H), 7.11 (d, 1H), 6.60 (s, 1H), 6.38 (b s, 1H), 4.25 (s, 2H), 3.94 (t, 2H), 3.88 (t, 2H), 2.77 (t, 2H), 2.63 (2xt, 4H), 2.24 (s, 6H), 2.18 (m, 2H), 2.07 (m, 2H), 1.90 (m, 2H), 1.50 (m, 4H).

Example 27

2,3,5,6,7,8-Hexahydro-5-[2'-methyl-4'-(2-oxopyrrolidin-1-yl)biphenyl-4-carbonyl]spiro[furo[2,3-g]quinoline-3,4'-piperidine]

This was prepared from 2,3,5,6,7,8-hexahydro-1'-methyl-5-[2'-methyl-4'-(2-oxopyrrolidin-1-yl)biphenyl-4-carbonyl]spiro[furo[2,3-g]quinoline-3,4'-piperidine] (E26) following a similar procedure to Example 18. The title compound was converted to its hydrochloride salt as a light brown solid.

¹H NMR (HCl salt) (250 MHz, d⁶DMSO) δ (ppm): 9.01 (br m, 1H), 8.65 (br m, 1H1), 7.62 (dd, 1H), 7.56 (d, 1H), 7.30 (m, 4H), 7.19 (d, 1H), 6.68 (s, 1H), 6.47 (b, 1H), 4.39 (s, 2H), 3.87 (t, 2H), 3.79 (t, 2H), 3.08 (m, 2H), 2.87 (m, 4H), 2.76 (t, 2H), 2.55 (m, 2H), 2.23 (s, 3H), 2.09 (m, 2H), 1.95 (m, 2H), 1.58 (m, 2H).

Example 28 cis-2',6'-dimethyl isomer of 5-[2'-Methyl-4'-(2-oxopyrrolidin-1-yl)biphenyl-4-carbonyl]-2,3,6,7-tetrahydro-1',2',6'-trimethylspiro[furo[2,3-f]indole-3,4'-piperidine]

A 3:1 isomeric mixture of the title compound was prepared from a 3:1 isomeric mixture of 2,3,6,7-tetrahydro-1',2',6'-trimethylspiro[furo[2,3-f]indole-3,4'-piperidine (D51, cis-2',6'-dimethyl isomer) and 2'-methyl-4'-(2-oxopyrrolidin-1-yl)biphenyl-4-carboxylic acid (D47) was converted to its hydrochloride salt and crystallised from ethyl acetate/ether.

¹H NMR (free base) (250 MHz, CDCl₃) δ (ppm): 8.52 (br s, 1H-isomer A), 8.10 (br m, 1H-isomer B), 7.70–7.47 (m, 4H), 7.45–7.33 (m, 2H), 7.30–7.20 (m, 1H), 6.71 (s, 1H-isomer A), 6.66 (s, 1H-isomer B), 4.43 (br s, 2H-isomer B), 4.21 (br s, 2H-isomer A), 4.14 (br t, 2H), 3.91 (t, 2H), 3.09 (t, 2H), 3.00 (br m, 2H), 2.64 (t, 2H), 2.54 (br s), 2.40–1.60 (m) including 2.30 (br s) and 2.20 (quintet, 2H), 1.35–1.15 (m, 6H).

Example 29

5-[2'-Methoxycarbonyl-4'-(2-oxopyrrolidin-1-yl)biphenyl-4-carbonyl]-1'-methyl-2,3,6,7-tetrahydrospiro[furo[2,3,f]indole-3,4'-piperidine]

The title compound was prepared from 2'-methoxycarbonyl-4'-(2-oxopyrrolidin-1-yl)biphenyl-4-carboxylic acid (D53) and 1'-methyl-2,3,6,7-tetrahydrospiro[furo[2,3-f]indole-3,4'-piperidine] (D7) following a similar procedure to Example 15 as an off-white powder (66%).

¹H NMR (250 MHz, CDCl₃) δ (ppm): 8.12 (br s, 1H), 8.05 (d, 1H), 7.94 (s, 1H), 7.59 (d, 2H), 7.42–7.31 (m, 3H), 6.65 (s, 1H), 4.4 (br s, 2H), 4.15–4.0 (m, 2H), 3.93 (t, 2H), 3.68 (s, 3H), 3.05 (t, 2H), 2.94–2.77 (m, 2H), 2.65 (t, 2H), 2.38–1.91 (m, 7H), 1.88–1.55 (m, 4H).

Example 30

5-[2'-Hydroxymethyl-4'-(2-oxopyrrolidin-1-yl)biphenyl-4-carbonyl]-1'-methyl-2,3,6,7-tetrahydrospiro[furo[2,3-f]indole-3,4'-piperidine]

Ethyl 2'-hydroxymethyl-4'-(2-oxopyrrolidin-1-yl)biphenyl-4-carboxylate (D54, 0.319 g, 0.94 mmol), t-butyldimethylsilyl chloride (TBDMS-Cl, 0.19 g, 1.26 mmol), 4-dimethylaminopyridine (DMAP, 0.03 g, 0.24 mmol) and triethylamine (0.26 ml, 1.86 mmol) were stirred in dichloromethane (10 ml) for 20 h. Further TBDMS-Cl and DMAP were then added to ensure complete reaction. After a further 24 h, the mixture was washed quickly with 0.5M HCl, followed by 10% Na₂CO₃; it was then dried (Na₂SO₄) and evaporated to give a nearly colourless oil (0.49 g). This material was then reacted with 1'-methyl-2,3,6,7-tetrahydrospiro[furo[2,3-f] indole-3,4'-piperidine] (D7) following a procedure similar to that of Example 18. The crude product was dissolved in dry THF, and stirred with excess tetrabutylammonium fluoride (1M in THF) for 3 h, diluted with ethyl acetate, washed with water and brine, dried (Na₂SO₄) and evaporated. Chromatography then gave the title compound as a colourless glass. This was converted to its hydrochloride salt.

¹H NMR (HCl salt) (200 MHz, d⁶DMSO) δ (ppm): 10.4 (b, 1H), 7.9 (m, 2H), 7.65 (m, 3H), 7.50 (d, 2H), 7.30 (d, 1H), 6.78 (s, 1H), 4.52 (s, 2H), 4.45 (s, 2H), 4.06 (t, 2H), 3.89 (t, 2H), 3.4 (m, 2H), 3.1 (m, 4H), 2.79 (s, 3H), 2.6 (m, 2H), 2.15 (m, 4H), 1.9 (m, 2H).

Example 31

5-[2'-Methoxymethyl-4'-(2-oxopyrrolidin-1-yl)biphenyl-4-carbonyl]-1'-methyl-2,3,6,7-tetrahydrospirolfuro[2,3-f]indole-3,4'-piperidine]

This was prepared from ethyl 2'-methoxymethyl-4'-(2-oxopyrrolidin-1-yl)biphenyl-4-carboxylate (D55) following a procedure similat to that of Example 15.

¹H NMR (250 MHz, CDCl₃) δ (ppm): 8.14 (b s, 1H), 7.78 (dd, 1H), 7.68 (d, 1H), 7.60 (d, 2H1), 7.43 (d, 2H), 7.32 (d, 1H), 6.67 (s, 1H), 4.39 (s, 2H), 4.35 (s, 2H), 4.10 (m, 2H), 3.94 (t, 2H), 3.37 (s, 3H), 3.08 (t, 2H), 2.88 (b, 2H), 2.64 (t, 2H), 2.33 (s, 3H) 2.20 (quintet, 2H), 2.05 (m, 4H), 1.75 (m, 2H).

Example 32

1'-tert-Butyl-5-[2'-methyl-4'-(2-oxopyrrolidin-1-yl)biphenyl-4-carbonyl]-2,3,6,7-tetrahydrospiro[furo[2, 3-f]indol-3,4'-piperidine]

The title compound was prepared from 1'-tert-butyl-2,3, 6,7-tetrahydrospiro[furo[2,3-f]indole-3,4'-piperidine) (D61) and 2'-methyl-4'-(2-oxopyrrolidin-1-yl)biphenyl-4-carboxylic acid (D47) using the method outlined in Example 15.

¹H NMR (200 MHz, CDCl₃) δ (ppm): 8.19 (br s, 1H), 7.65–7.43 (m, 4H), 7.35 (d, 2H), 7.22 (d, 1H), 6.65 (s, 1), 4.38 (s, 2H), 4.24–4.01 (m, 2H), 3.9 (t, 2H), 3.17–2.9 (m, 4H), 2.63 (t, 2H), 2.3 (s, 3H), 2.28–1.95 (m, 6H), 1.85–1.62 (m, 2H), 1.1 (s, 9H).

Example 33

2,3-Dihydro-1'-methyl-5-[2'-methyl-4'-(2-oxopyrrolidin-1-yl)biphenyl-4-carbonyl]spiro[furo[3,2-f]indole3,4'-piperidine]

A stirred suspension of 2'-methyl-4'-(2-oxopyrrolidin-1-yl)biphenyl-4-carboxylic acid (0.26 ml, 0.0030 mole) and DMF (1 drop) and kept at 25° C. for 1 hr. The resulting solution was washed rapidly with NaHCO₃ solution, then dried (Na₂SO₄) and concentrated in vacuo to afford the acid chloride as a yellow solid (0.75 g). A solution of 2,3-dihydro-1'-methylspiro[furo[3,2-f]indole-3,4'-piperidine)

(D68, 290 mg, 1.2 mmole) in dry THF (10 ml) was added dropwise over 10 minutes to a stirred solution of ethylmagnesium bromide (1.3 mmole) in dry THF (8 ml) at room temp. under argon and the resulting mixture heated at 40° C. for 30 minutes. The dark green solution was then cooled to 0° C. and treated dropwise over 5 minutes with a solution of the above acid chloride (630 mg, 2.0 mmole) in dry THF (5 ml). The reaction mixture was stirred at room temp. for 1.5 h, then concentrated under vacuum. The residue was treated with 10% $Na_2CO_3$ solution and extracted with dichloromethane. The extract was dried ($Na_2SO_4$), concentrated in vacuo and the residue chromatographed on silica gel eluting with 0–10% methanol/chloroform. This afforded the 1,3-diaroylated product, which was treated with methanol (15 ml), 10% NaOH solution (15 ml) and dichloromethane (15 ml) and the two-phase system stirred at room temp. for 2 h. The mixture was extracted with dichloromethane (2×30 ml) and the combined extract dried ($Na_2SO_4$) and concentrated in vacuo. The residue was purified by preparative plate TLC on silica gel eluting with 15% methanol/chloroform to afford the title compound (80 mg, 13%). This was converted to its hydrochloride salt, which crystallised from acetone as a white solid.

$^1$H NMR (free base) (250 MHz, $CDCl_3$) δ (ppm): 8.21 (s, 1H), 7.83 (d, 2H), 7.60 (d, 1H), 7.58–7.48 (m, 2H), 7.40 (d, 2H), 7.28 (d, 1H), 6.85 (s, 1H), 4.45 (s, 2H), 3.93 (t, 2H), 2.96–2.84 (m, 2H), 2.63 (t, 2H), 2.35 (s, 3H), 2.32 (s, 3H), 2.30–1.95 (m, 6H), 1.87–1.75 (m, 2H).

PHARMACOLOGICAL DATA

5-HT 1B AND 5-HT 1D RECEPTOR BINDING

CHO cells expressing 5-HT 1D receptors (0.563×10$^8$ cells/ml) were homogenised in Tris buffer and stored in 1 ml aliquots. CHO cells expressing 5-HT 1B receptors (4×10$^7$cells/ml) were homogenised in Tris buffer and stored in 1.5 ml aliquots. 0.4 ml of a cell suspension was incubated with [$^3$H-5-HT (4 nM) in Tris Mg HCl buffer (pH 7.7) and test drug, at 37° C. for 45 minutes. Each test drug was tested at 10 concentrations (0.01 mM to 0.3 nM final concentration), with non-specific binding defined using 0.01 mM 5-HT. The total assay volume was 0.5 ml. Incubation was stopped by rapid filtration using a Packard Filtermate (filters pre-soaked in 0.3% polyethylenimine) and radioactivity measured by Topcount scintillation counting. pKi values were calculated from the IC$_{50}$ generated by an iterative least squares curve fitting programme.

Examples 1, 3, 4, 7, 8, 9, 14, 24, 28, and 33 had pKi values >8.0 at 5-HT 1D beta receptors.

What is claimed is:

1. A compound of formula (I) or a pharmaceutically acceptable salt or N-oxide thereof:

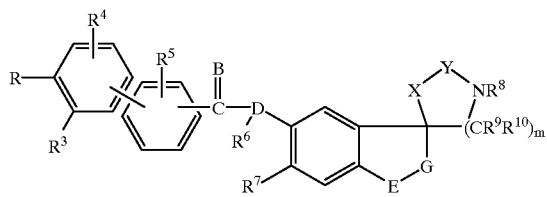

(I)

in which
R is a substituted lactam ring of formula (i):

(i)

where Z is oxygen or sulphur;
p is 1; and
P is a substituted or unsubstituted bicyclic ring containing one or two heteroatoms; or P is an unsubstituted or substituted 5- to 7-membered saturated ring containing one or two heteroatoms;
$R^4$ and $R^5$ are independently hydrogen halogen $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkylO$C_{1-6}$alkyl, acyl, aryl, acyloxy, hydroxy, nitro, trifluoromethyl, cyano, $CO_2R^{11}$, $CONR^{12}R^{13}$, $NR^{12}R^{13}$ where $R^{11}$, $R^{12}$ and $R^{13}$ are independently hydrogen or $C_{1-6}$alkyl, or $R^4$ and $R^5$ together form a group —$(CH_2)_r$—$R^{14}$—$(C_2)_s$— where $R^{14}$ is O, S, $CH_2$ or $NR^{15}$ where $R^{15}$ is hydrogen or $C_{1-6}$alkyl and r and s are independently 0, 1 or 2;
B is oxygen or sulphur;
D is nitrogen;
$R^6$ together with $R^7$ forms a group —A— where A is $(CR^{16}R^{17})_t$ where t is 2 and $R^{16}$ and $R^{17}$ are independently hydrogen or $C_{1-6}$alkyl;
$R^8$ is hydrogen, $C_{1-6}$alkyl, $C_{3-6}$cycloalkyl, $C_{2-6}$alkenyl or $C_{1-6}$alkylC$_{3-6}$cycloalkyl;
$R^9$ and $R^{10}$ are independently hydrogen or $C_{1-6}$alkyl;
E is oxygen;
G is $(CR^{21}R^{22})_n$ where $R^{21}$ and $R^{22}$ are independently hydrogen or $C_{1-6}$alkyl and n is 1;
X and Y are independently $CR^9R^{10}$ where $R^9$ and $R^{10}$ are as defined above; and
m is 2.

2. A compound according to claim 1 in which $R^4$ is $C_{1-6}$alkyl.

3. A compound according to claim 1 in which $R^5$ is hydrogen.

4. A compound according to claim 1 in which E is oxygen and G is $CH_2$.

5. A compound according to claim 1 in which X and Y are both $CH_2$.

6. A compound according to claim 1 in which $R^9$ and $R^{10}$ are both hydrogen.

7. A compound according to claim 1 which is:
1'-methyl-5-[2'-methyl-4'-(2-oxo-1-piperidinyl)biphenyl-4-carbonyl]-2,3,6,7-tetrahydrospiro [furo[2,3-f]indole-3,4'-piperidine],
5-[4'-(4,5-dihydro-2-oxooxazol-3-yl)-2'-methylbiphenyl-4-carbonyl]-1'-methyl-2,3,6,7-tetrahydrospiro[furo[2,3-f]indole-3,4'-piperidine],
5-(4'-acetamido-2'-methylbiphenyl-4-carbonyl)-1'-metbyl-2,3,6,7-tetrahydrospiro[furo[2,3-f]indole-3,4'-piperidine],
1'-methyl-5-[2'-methyl-4'-(2-thioxo-1-pyrrolidinyl)biphenyl-4-carbonyl]-2,3,6,7-tetrahydrospiro[furo[2,3-f]indole-3,4'-piperidine],
5-[4'-(1,1-dioxo-2,3,4,5-tetrahydroisothiazol-2-yl)-2'-methylbiphenyl-4-carbonyl]-1-'-methyl-2,3,6,7-tetrahydrospiro[furo[2,3-f]indole-3,4'-piperidine], 5-[4'-(4,5-dihydro-2-oxoimidazol-1-yl)-2'-methylbiphenyl-4-carbonyl]-1'-methyl-2,3,6,7-tetrahydrospiro[furo[2,3-f]indole-3,4'-piperidine], 5-[4'-(4,5-dihydro-3-methyl-2-oxoimidazol-1-yl)-2'-methylbiphenyl-4-carbonyl]-1'-methyl-2,3,6,7-tetrahydrospiro[furo[2,3-f]indole-3,4'-piperidine], 1'-methyl-5-[2'-methyl-4'-(3-methyl-2-oxopyrrolidin-1-yl)biphenyl-4-carbonyl]-2,3,6,7-tetrahydrospiro[furo[2,3-f]indole-3,4'-piperidine], 5-[4'-(3,3-dimethyl-2-oxopyrrolidin-1-yl)-2'-methylbiphenyl-4-carbonyl]-1'-methyl-2,3,6,7-tetrahydrospiro[furo[2,3-f]indole-3,4'-piperidine], 5-[4'-(2,3-dihydro-1-oxoisoindol-2-yl)-2'-methylbiphenyl-4-carbonyl]-1'-methyl-2,3,6,7-tetrahydrospiro[furo[2,3-f]indole-3,4'-piperidine], 5-[2,3 7-dimethyl4'-(2-oxopyrrolidin-1-yl)biphenyl-4-carbonyl]-1-methyl-2,3,6,7-tetrahydrospiro[furo[2,3-f]indole-3,4'-piperidine], 1'-methyl-5-[4'-(2-oxo-1-pyrrolidinyl)-2'-trifluoromethylbiphenyl-4-carbonyl]-2,3,6,7-tetrahydrospiro[furo[2,3-f]indole-3,4'-piperidine], 5-[2'-chloro-4'-(2-oxo-1-pyrrolidinyl)biphenyl-4-carbonyl]-1'-methyl-2,3,6,7-tetrahydrospiro[furo[2,3-f]indole-3,4'-piperidine], 5-[4-(1-acetyl-1,2,3,4-tetrahydroqainolin-6-yl)-3-methylbenzoyl]-1'-methyl-2,3,6,7-tetrahydrospiro[furo[2,3-f]indole-3,4'-piperidine], 5-4-(1-acetyl-2,3-dihydroindol-5-yl)-3-methylbenzoyl]-1'-methyl-2,3,6,7-tetrahydrospiro [furo[2,3-f]indole-3,4'-piperidine], 1'-methyl-5-(2'-methyl-4'-(2-oxo-1H-pyrazin-1-yl) biphenyl-4-carbonyl]-2,3,6,7-tetrahydrospiro [furo[2,3-f]indole-3,4'-piperidine], 5-[2'-methyl-4'-(2-oxopyrrolidin-1-yl)biphenyl-4-carbonyl]-2,3,6,7-tetrahydrospiro[furo[2,3-f]indole-3,4-piperidine], 1'-ethyl-5-(2'-methyl-4'-(2-oxopyrrolidin-1-yl)biphenyl-4-carbonyl]-2,3,6,7-tetrabydrospiro[furo[2,3-f]indole-3,4'-piperidire], 5-2'-methyl-4'-(2-oxopyrrolidin-1-yl)biphenyl-4-carbonyl]-1'-n-propyl-2,3,6,7-tetrabydrospiro[furo[2,3-f]indole-3,4'-piperidine], 1'-isopropyl-5-[2'-methyl-4'-(2-oxopyrrolidin-1-yl) biphenyl-4-carbonyl]-2,3,6,7-tetrahydrospiro[furo[2,3-f]indole-3,4'-piperidine], 1'-n-butyl-5-[2'-methyl-4'-(2-oxopyrrolidin-1-yl) biphenyl-4-carbonyl]-2,3 6,7-tetrahydrospiro[furo[2,3-f]indole-3,4'-piperidine], 1'-cyclopropylmethyl-5-[2'-methyl-4'(2-oxopyrrolidin-1-yl)biphenyl-4-carbonyl]-2,3,6,7-tetrahydrospiro[furo [2,3-f]indole-3,4'-piperidine], 1'-allyl-5-[2'-methyl-4'-(2-oxopyrrolidin-1-yl)biphenyl-4-carbonyl]-2,3,6,7-tetrahydrospiro[furo[2,3-f]indole-3,4'-piperidine], 1'-cyclopentyl-5-[2'-methyl-4'-(2-oxopyrrolidin-1-yl) biphenyl-4-carbonyl]-2,3,6,7-tetrahydrospiro[furo[2,3-f]indole-3 4'-piperidine], 5-[2'-methoxycarbonyl-4'-(2-oxopyrrolidin-1-yl) biphenyl-4-carbonyl]-1'-methyl-2,3,6,7-tetrahydrospiro[furo[2,3,f]indole-3,4'-piperidine], 5-2'-hydroxymethyl-4'-(2-oxopyrrolidin-1-yl)biphenyl-4-carbonyl]-1'-methyl-2,3,6,7-tetrahydrospiro[furo[2,3-f]indole-3,4'-piperidine], 5-[2'-methoxymethyl-4'-(2-oxopyrrolidin-1-yl) biphenyl4-carbonyl]-1'-methyl-2,3,6,7-tetrahydrospiro [furo[2,3-f]indole-3,4'-piperidine], 1'-tert-butyl-5-[2'-methyl-4'-(2-oxopyrrolidin-1-yl) biphenyl-4-carbonyl]-2,3,6,7-tetrahydrospiro[furo[2,3-f]indole-3,4'-piperidine], or a pharmaceutically acceptable salt or N-oxides thereof.

8. A compound according to claim 1 which is:

5-[2'-methyl4'-(2-oxo-1-pyrrolidinyl)biphenyl-4-carbonyl]-1'-methyl-2,3,6,7-tetrahydrospiro[furo[2,3-f]indole-3,4'-piperidine], 1'-methyl-5-[2'-methyl-4'-(3-methyl-2-oxopyrrolidin-1-yl)biphenyl-4-carbonyl]-2,3,6,7-tetrahydrospiro[furo [2,3-f]indole-3,4'-piperidine], 1'-isopropyl-5-[2'-methyl-4'-(2-oxopyrrolidin-1-yl) biphenyl-4-carbonyl]-2,3,6,7-tetrahydrospiro[furo[2,3-f]indole-3,4'-piperidine], or a pharmaceutically acceptable salt thereof.

9. A pharmaceutical composition which comprises a compound according to claim 1 in association with a pharmaceutically acceptable carrier or excipient.

10. A method of treating depression, seasonal effective disorder, dysthymia, anxiety, panic disorder, agoraphobia, social phobia, obsessive compulsive disorder, post-traumatic stress disorder, dementia, amnesia, age-associated memory impairment, anorexia nervosa, bulimia nervosa, Parkinson's disease, dementia in Parkinson's disease, neuroleptic-induced Parkinsonism, tardive dyskinesias which method involves treating a patient in need thereof with a therapeutically effective amount of a compound of claim 1.

11. A method of treating hyperprolactinaemia, vasospasm, hypertension, hypothermia and sexual dysfunction which method involves treating a patient in need thereof with a therapeutically effective amount of a compound of claim 1.

12. A process for the preparation of a compound of formula (I) which comprises:

(a) for compounds of formula (I) where D is nitrogen reaction of a compound of formula (II):

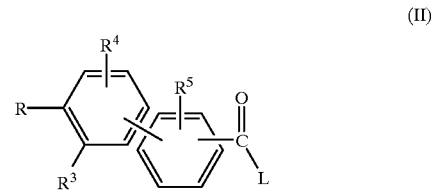

(II)

in which R, $R^3$, $R^4$ and $R^5$ are groups as defined in formula (I) or protected derivatives thereof and L is a leaving group with a compound of formula (III):

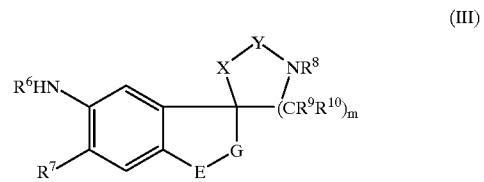

(III)

wherein $R^6$, $R^7$, $R^8$, $R^9$, $R^{10}$, E, G, X, Y, and m are groups as defined in formula (I) or protected derivatives thereof, or (b) for compounds of formula (I) where D is carbon, B is oxygen and $R^6/R^7$ is $=CR^{16}O$, $=CR^{16}S$ or $=CR^{16}$—

NR$^{17}$ reaction of a compound of formula (II) as defined above where L is chloro with a compound of formula (IV):

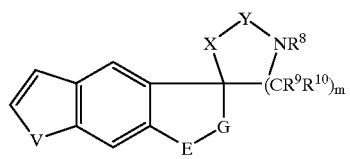

(IV)

wherein R$^6$, R$^7$, R$^8$, R$^9$, R$^{10}$, E, G, X, Y, and m are groups as defined in formula (I) or protected derivatives thereof and V is NR$^{17}$, O or S, and optionally after (a) or (b) in any order, removing any protecting groups, converting a compound of formula (I) into another compound of formula (I), forming a pharmaceutically acceptable salt.

* * * * *